United States Patent [19]
Panescu et al.

[11] Patent Number: 5,485,849
[45] Date of Patent: Jan. 23, 1996

[54] SYSTEM AND METHODS FOR MATCHING ELECTRICAL CHARACTERISTICS AND PROPAGATION VELOCITIES IN CARDIAC TISSUE

[75] Inventors: Dorin Panescu, Sunnyvale; David K. Swanson, Mountain View, both of Calif.

[73] Assignee: EP Technologies, Inc., Sunnyvale, Calif.

[21] Appl. No.: 189,445

[22] Filed: Jan. 31, 1994

[51] Int. Cl.⁶ ............................................. A61C 5/04
[52] U.S. Cl. .................... 128/699; 128/696; 128/642; 607/119
[58] Field of Search ................................ 128/695, 696, 128/702, 642, 699; 607/115, 116, 119, 122

[56] References Cited

U.S. PATENT DOCUMENTS

| | | |
|---|---|---|
| 4,380,237 | 4/1983 | Newbower . |
| 4,522,212 | 6/1985 | Gelinas et al. . |
| 4,628,937 | 12/1986 | Hess et al. ........................... 128/642 |
| 4,674,518 | 6/1987 | Salo . |
| 4,699,147 | 10/1987 | Chilson et al. . |
| 4,852,580 | 8/1989 | Wood . |
| 4,911,174 | 3/1990 | Pederson et al. . |
| 5,041,973 | 8/1991 | Lebron et al. ..................... 364/413.05 |
| 5,058,583 | 10/1991 | Geddes et al. . |
| 5,092,339 | 3/1992 | Geddes et al. . |
| 5,109,870 | 5/1992 | Silny et al. . |
| 5,137,019 | 8/1992 | Pederson et al. . |
| 5,156,151 | 10/1992 | Imran . |
| 5,195,968 | 3/1993 | Lundquist et al. . |
| 5,197,467 | 3/1993 | Steinhaus et al. . |
| 5,224,475 | 7/1993 | Berg et al. . |
| 5,228,442 | 7/1993 | Imran ................................... 128/642 |
| 5,239,999 | 8/1993 | Imran . |
| 5,246,008 | 9/1993 | Mueller . |
| 5,255,679 | 10/1993 | Imran . |
| 5,279,299 | 1/1994 | Imran . |
| 5,282,840 | 2/1994 | Hudrlik . |
| 5,293,869 | 3/1994 | Edwards et al. . |
| 5,297,549 | 3/1994 | Beatty et al. ........................... 128/642 |
| 5,309,910 | 5/1994 | Edwards et al. . |
| 5,313,943 | 5/1994 | Houser et al. . |
| 5,324,284 | 6/1994 | Imran ...................................... 606/15 |
| 5,341,807 | 8/1994 | Nardella . |
| 5,345,936 | 9/1994 | Pomeranz et al. . |
| 5,383,917 | 1/1995 | Desai et al. . |
| 5,397,339 | 3/1995 | Desai . |

OTHER PUBLICATIONS

Michael A. Fallert, MD, Myocardial Electrical Impedance Mapping of Ischemic Sheep Hearts and Healing Aneurysms, Circulation vol. 87, No. 1 Jan. 1993, 199–207.

*Primary Examiner*—William E. Kamm
*Assistant Examiner*—Marianne Parker
*Attorney, Agent, or Firm*—Ryan, Maki & Hohenfeldt

[57] ABSTRACT

Systems and methods examine heart tissue morphology using three or more spaced apart electrodes, at least two of which are located within the heart in contact with endocardial tissue. The systems and methods transmit electrical current through a region of heart tissue lying between selected pairs of the electrodes, at least one of the electrodes in each pair being located within the heart. The systems and methods derive the electrical characteristic of tissue lying between the electrode pairs based, at least in part, upon sensing tissue impedances. The systems and methods also sense the timing of local depolarization events in the tissue in which impedance is sensed and derive therefrom the propagation velocities of the sensed depolarization events. The systems and methods match the derived tissue electrical characteristics with the derived propagation velocities in spatial relation to the electrodes to characterize the morphology of the contacted heart tissue. This matching provides precise differentiation between regions of infarcted heart tissue and healthy heart tissue.

19 Claims, 26 Drawing Sheets

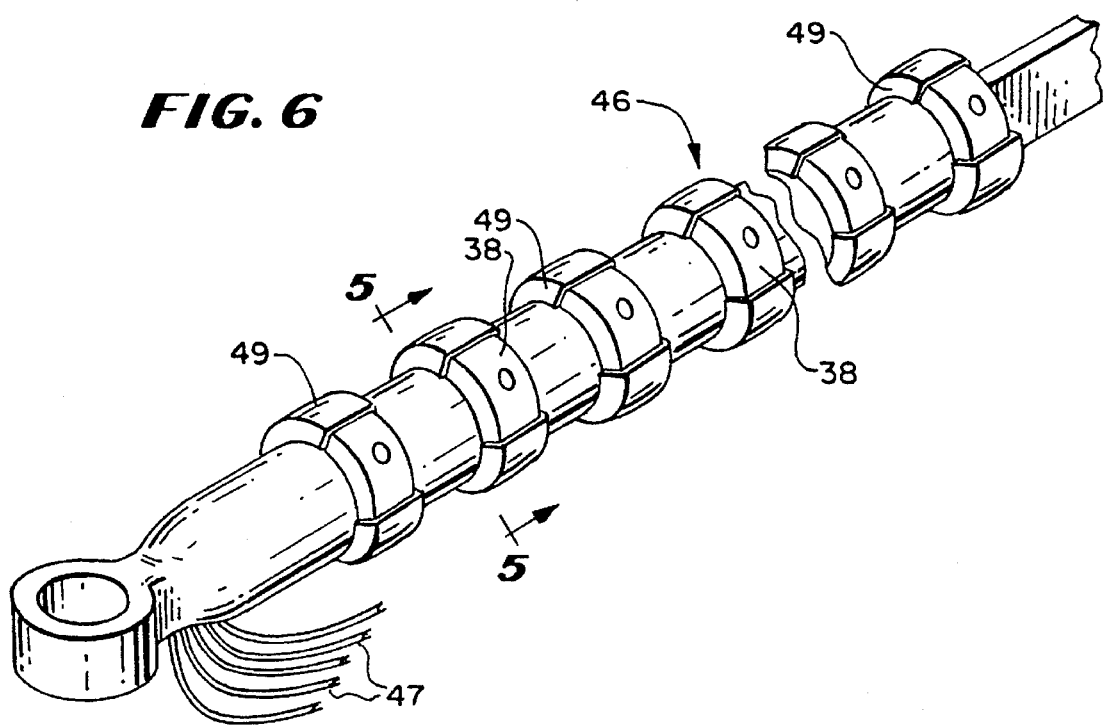

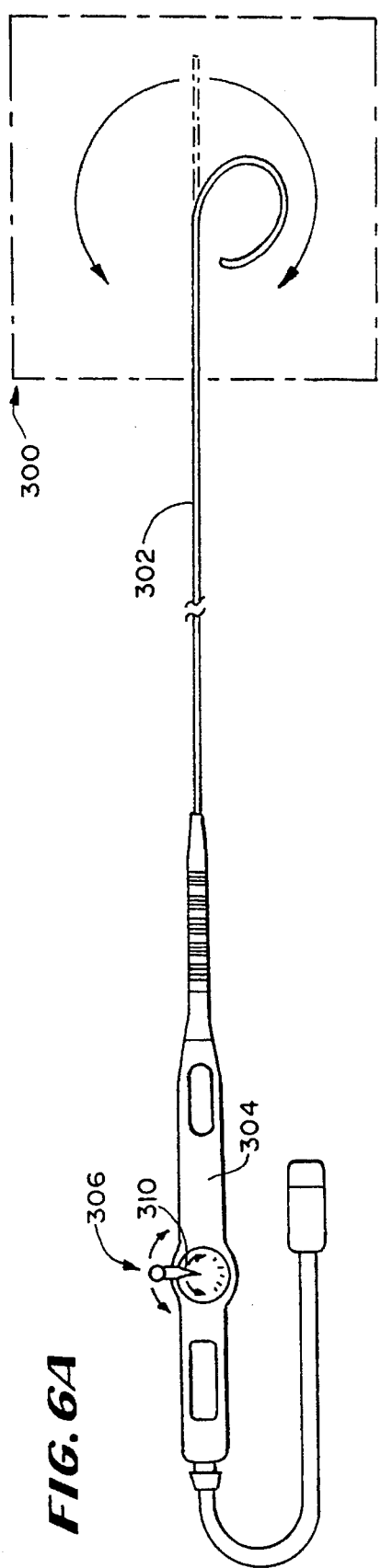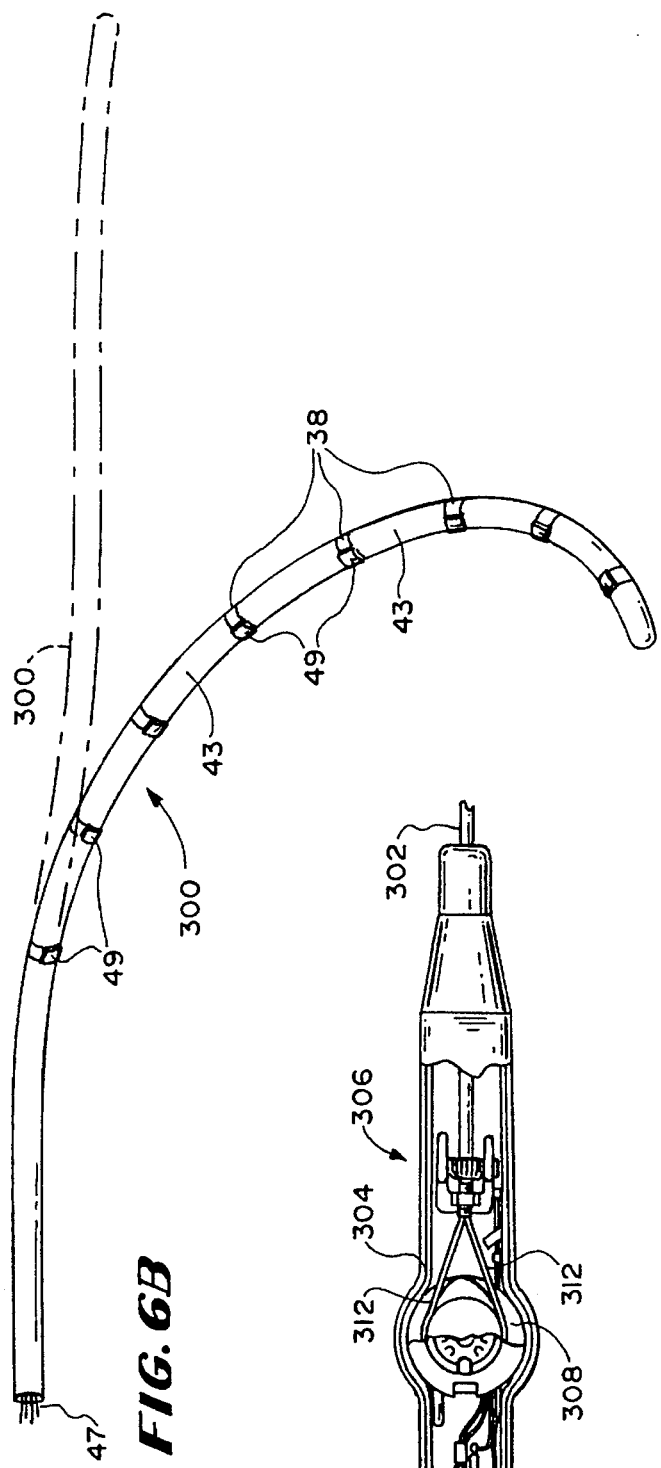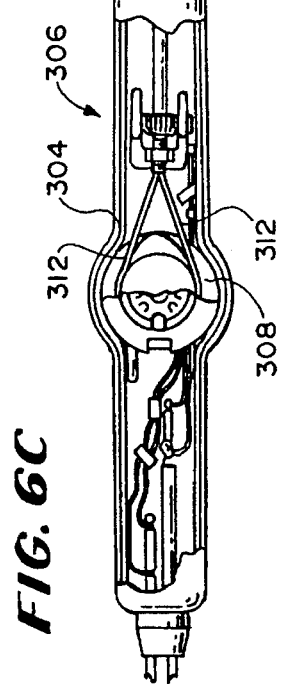
FIG. 6A
FIG. 6B
FIG. 6C

SYSTEM AND METHODS FOR MATCHING ELECTRICAL CHARACTERISTICS AND PROPAGATION VELOCITIES IN CARDIAC TISSUE

RELATED APPLICATION

This application claims the benefit of prior filed copending U.S. patent application Ser. No. 08/188,242, Jan. 28, 1994, entitled "Systems and Methods for Deriving and Displaying the Propagation Velocities of Electrical Events in the Heart."

1. Field of the Invention

The invention relates to systems and methods for mapping the interior regions of the heart for treatment of cardiac conditions.

2. Background of the Invention

Physicians examine the propagation of electrical impulses in heart tissue to locate aberrant conductive pathways. The aberrant conductive pathways constitute peculiar and life threatening patterns, called dysrhythmias. The techniques used to analyze these pathways, commonly called "mapping," identify regions in the heart tissue, called foci, which are ablated to treat the dysrhythmia.

Conventional cardiac tissue mapping techniques use multiple electrodes positioned in contact with epicardial heart tissue to obtain multiple electrograms. Digital signal processing algorithms convert the electrogram morphologies isochronal displays, which depict the propagation of electrical impulses in heart tissue over time. These conventional mapping techniques require invasive open heart surgical techniques to position the electrodes on the epicardial surface of the heart.

Furthermore, conventional epicardial electrogram processing techniques used for detecting local electrical events in heart tissue are often unable to interpret electrograms with multiple morphologies. Such electrograms are encountered, for example, when mapping a heart undergoing ventricular tachycardia (VT). For this and other reasons, consistently high correct foci identification rates (CIR) cannot be achieved with current multi-electrode mapping technologies.

Researchers have taken epicardial measurements of the electrical resistivity of heart tissue. Their research indicates that the electrical resistivity of infarcted heart tissue is about one-half that of healthy heart tissue. Their research also indicates that ischemic tissue occupying the border zone between infarcted tissue and healthy tissue has an electrical resistivity that is about two-thirds that of healthy heart tissue. See, e.g., Fallert et al., "Myocardial Electrical Impedance Mapping of Ischemic Sheep Hearts and Healing Aneurysms," *Circulation*, Vol. 87, No. 1, January 1993, 199–207.

This observed physiological phenomenon, when coupled with effective, non-intrusive measurement techniques, can lead to cardiac mapping systems and procedures with a CIR better than conventional mapping technologies.

SUMMARY OF THE INVENTION

A principal objective of the invention is to provide improved probes and methodologies to examine heart tissue morphology quickly, accurately, and in a relatively non-invasive manner.

One aspect of the invention provides systems and methods for examining heart tissue morphology using at least three spaced apart electrodes, at least two of which are located in contact with a region of heart tissue. The systems and methods transmit electrical current in a first path through the region of heart tissue between a first pair of the electrodes. The systems and methods transmit electrical current in a second path through heart tissue in the region between a second pair of the electrodes. The systems and methods derive from the electrical current transmissions tissue electrical characteristics based, at least in part, upon sensing the impedances of the tissue lying in the first and second paths.

This electrical characteristic (called the "E-Characteristic") can be directly correlated to tissue morphology. A low relative E-Characteristic indicates infarcted heart tissue, while a high relative E-Characteristic indicates healthy heart tissue. Intermediate E-Characteristic values indicate the border of ischemic tissue between infarcted and healthy tissue.

How the E-Characteristic is expressed depends upon how the electrical current is transmitted by the electrode pair through the heart tissue.

When one of the electrodes in the pair comprises an indifferent electrode located outside the heart (i.e., a unipolar arrangement), the E-Characteristic is expressed in terms of tissue impedance (in ohms). When both electrodes in the pair are located inside the heart (i.e., a bipolar arrangement), the E-Characteristic is expressed in terms of tissue resistivity (in ohm-cm).

The systems and methods also sense the timing of local depolarization events in the tissue in which impedance is sensed and derive therefrom the propagation velocities of the sensed depolarization events. The systems and methods match the derived tissue electrical characteristics with the derived propagation velocities in spatial relation to the electrodes to characterize the morphology of the contacted heart tissue.

This matching in effect matches electrogram morphologies with tissue E-Characteristics. This matching provides more precise differentiation between regions of infarcted heart tissue and healthy heart tissue than conventional systems and methodologies.

In a preferred embodiment, the systems and methods normalize the derived tissue electrical characteristics and the derived propagation velocities in spatial relation to the electrodes. In this embodiment, the systems and methods match the normalized derived electrical characteristics with the normalized derived propagation velocities in spatial relation to the electrodes.

In a preferred embodiment, the system and method apply two dimensional matched filtering to the normalized derived tissue electrical characteristics using the normalized propagation velocities as a template, or vice versa.

In a preferred embodiment, the matched values range in value in spatial relation to the electrodes. In this embodiment, systems and methods normalize the value range to a normalized range of 0.0 to 1.0 in spatial relation to the electrodes by dividing each matched value in the value range by the maximum matched value in the value range. In this embodiment, the systems and methods output the normalized matched values in groups of equal matched values in spatial relation to the electrodes.

These normalized matching techniques make possible the mapping of heart tissue to aid in the identification of possible tissue ablation sites.

Other features and advantages of the inventions are set forth in the following Description and Drawings, as well as in the appended Claims.

BRIEF DESCRIPTION OF THE DRAWINGS

FIG. 6 is an enlarged perspective view of an alternative embodiment of an electrode carrying spline that can be associated with the probe shown in FIG. 1;

FIGS. 6A to 6C and associated catheter tube are views of a flexible electrode support body that can carry the electrodes and deployed in the heart according to the invention;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
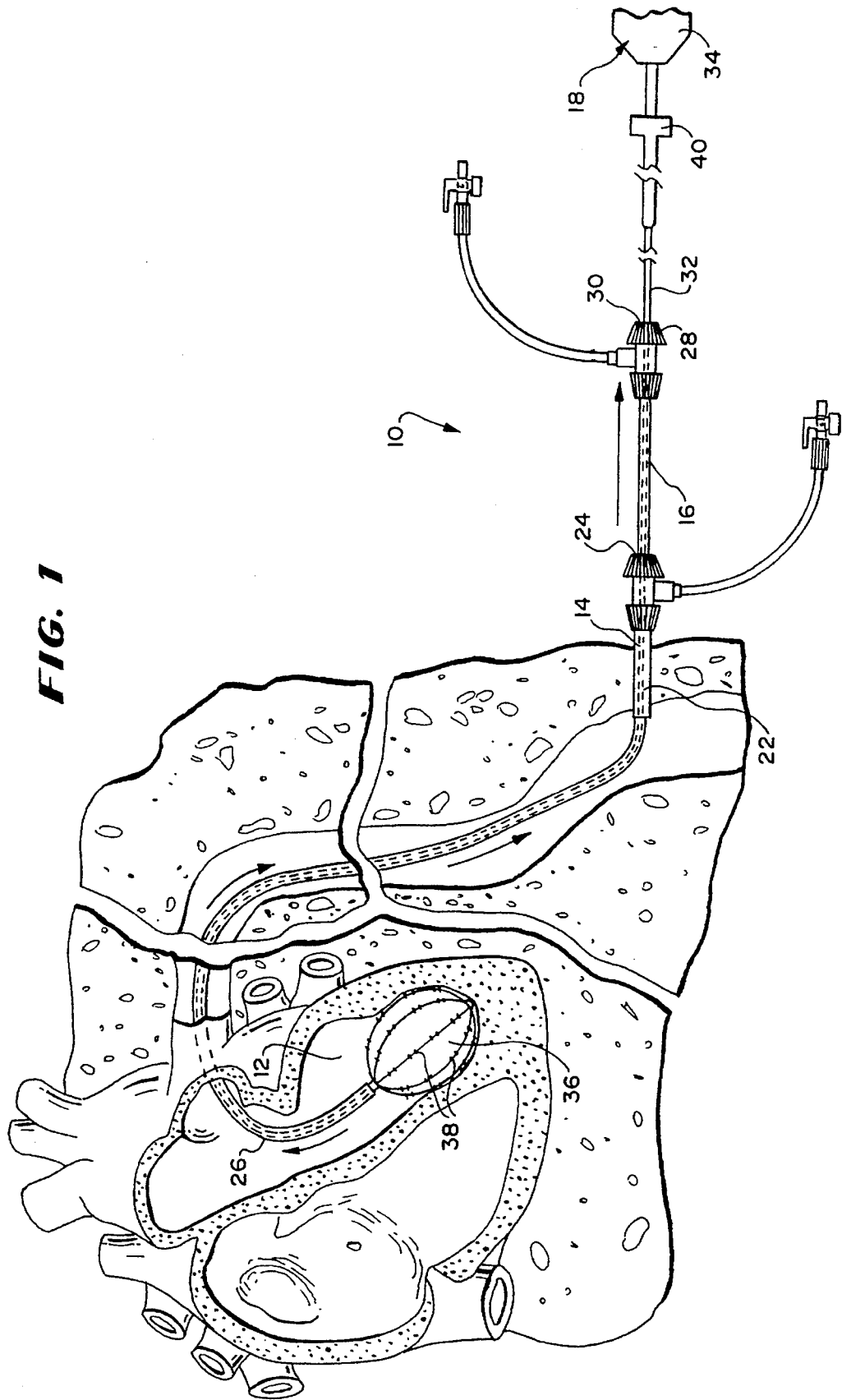
FIG. 1 is a plan view, with portions in section, of a system for examining and mapping heart tissue morphology according to the features of the invention, shown deployed for use within the heart.
Figure 2:
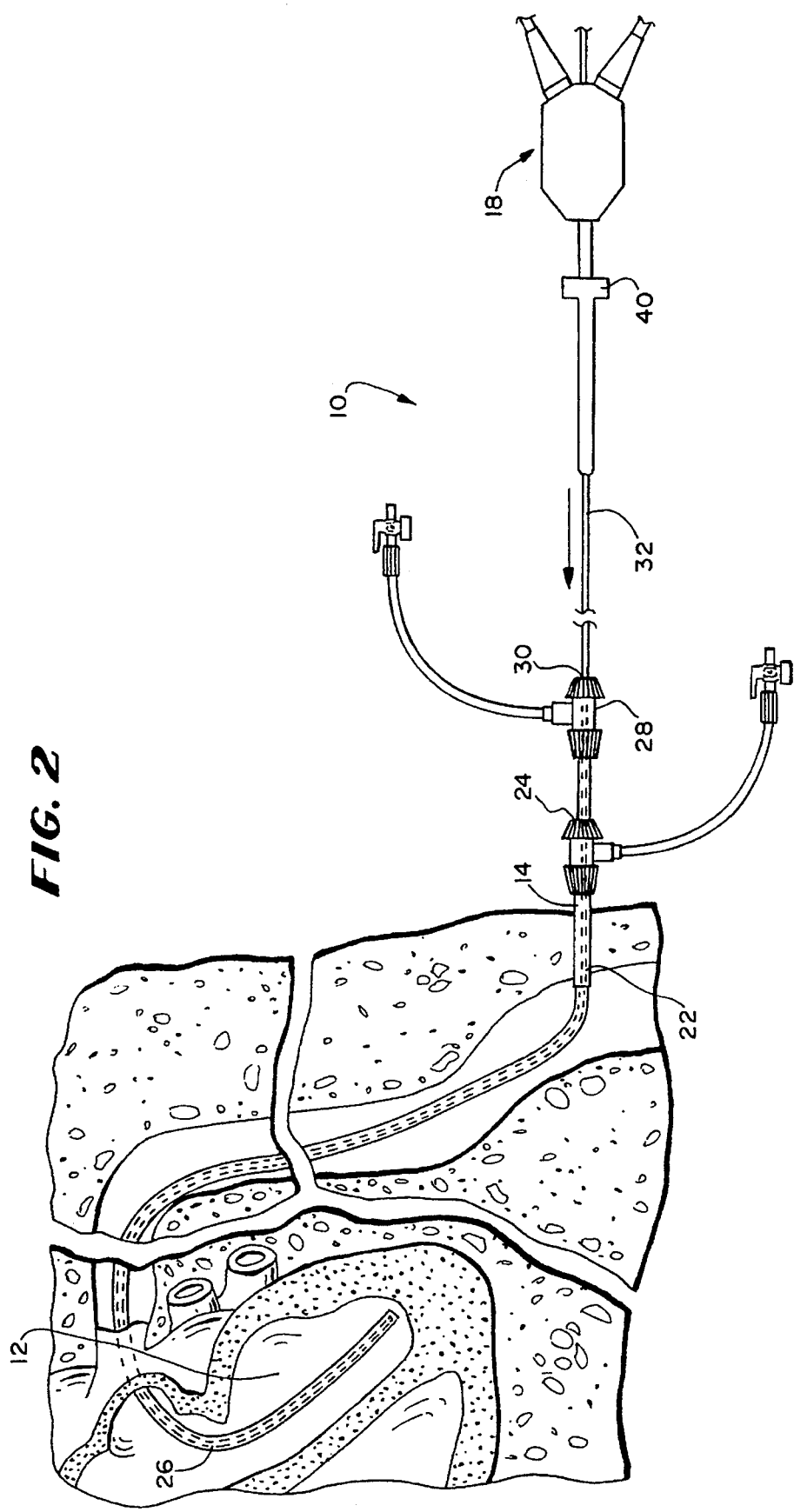
FIG. 2 is a plan view, with portions in section, of the system shown in FIG. 1 in the process of being deployed for use within the heart.
Figure 3:
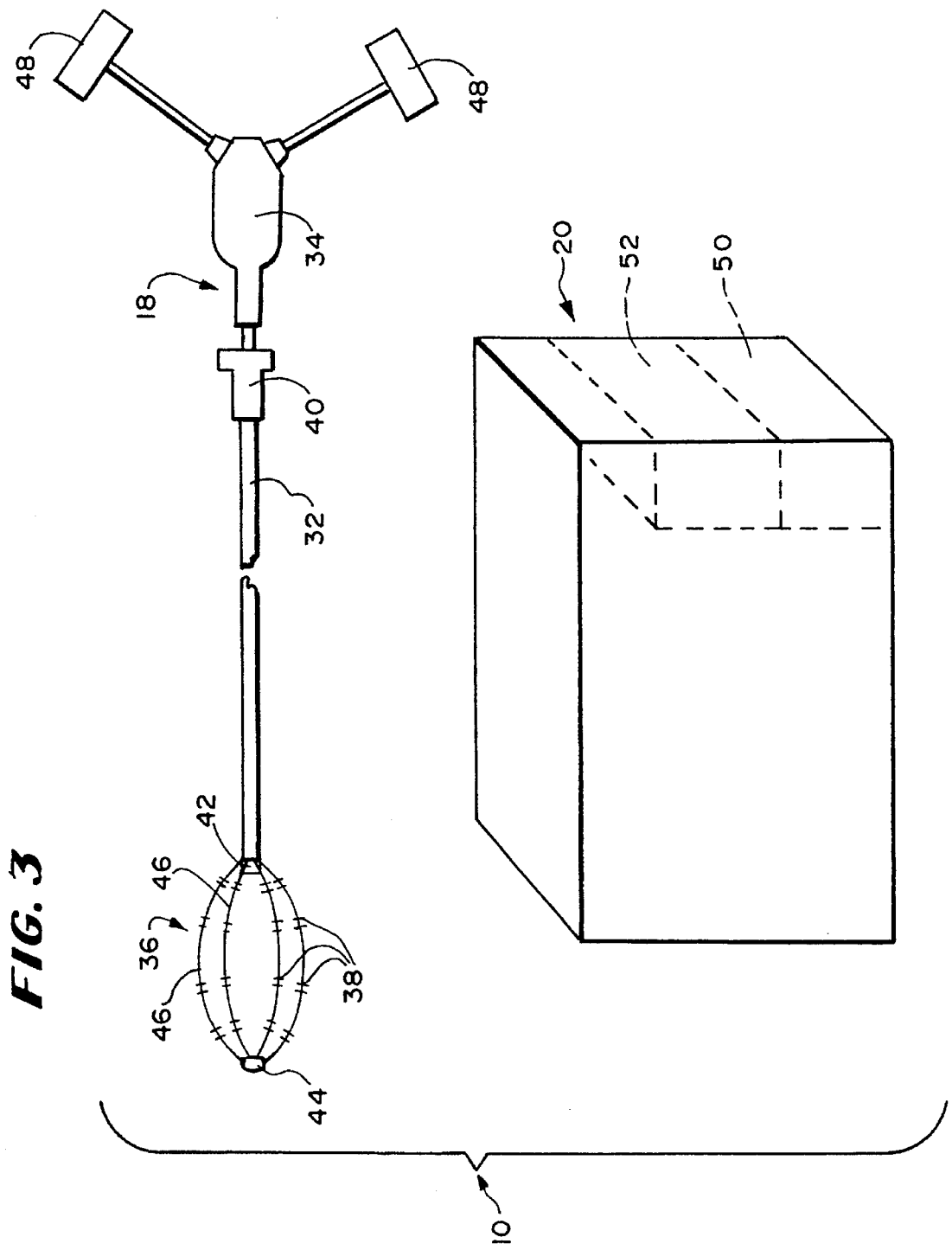
FIG. 3 is a view of the mapping probe and process controller associated with the system shown in FIG. 1.

FIGS. 1 to 3 show the components of a system 10 for examining heart tissue morphology. FIG. 1 shows the system 10 deployed and ready for use within a selected region 12 inside a human heart.

As FIGS. 1 and 2 show, deployment of the system 10 does not require invasive open heart surgical techniques. Instead, the system 10 includes an introducer 14 and an outer guide sheath 16 that together direct a multiple electrode probe 18 into the selected region 12 within the heart through a selected vein or artery. FIG. 3 shows the probe 18 in its entirety.

The physician uses the probe 18 in association with a process controller 20 (see FIG. 3) to take multiple, sequential measurements of the transmission of electrical current by heart tissue. From these, the electrical characteristic of the tissue is derived.

This electrical characteristic (called the "E-Characteristic") can be directly correlated to tissue morphology. A low relative E-Characteristic indicates infarcted heart tissue, while a high relative E-Characteristic indicates healthy heart tissue. Intermediate E-Characteristic values indicate the border of ischemic tissue between infarcted and healty tissue.

In the illustrated and preferred embodiment, these measurements are used to assist the physician in identifying appropriate ablation sites within the heart.

How the E-Characteristic is expressed depends upon how the electrical current is transmitted by an electrode pair through the heart tissue.

When one of the electrodes in the pair comprises an indifferent electrode located outside the heart (i.e., a unipolar arrangement), the E-Characteristic is expressed in terms of tissue impedance (in ohms). When both electrodes in the pair are located inside the heart (i.e., a bipolar arrangement), the E-Characteristic is expressed in terms of tissue resistivity (in ohm-cm).

FIG. 1 and the other figures generally show the system 10 deployed in the left ventricle of the heart. Of course, the system 10 can be deployed in other regions of the heart, too. It should also be noted that the heart shown in the Figures is not anatomically accurate. The Figures show the heart in diagrammatic form to demonstrate the features of the invention.

I. NON-INVASIVE SYSTEM DEPLOYMENT

As FIG. 1 shows, the introducer 14 has a skin-piercing cannula 22. The cannula 22 establishes percutaneous access into the selected vein or artery (which is typically the femoral vein or artery). The other end of the introducer 14 includes a conventional hemostatic valve 24.

The physician advances the outer guide sheath 16 through the introducer 14 through the vein or artery into the selected heart chamber 12. The hemostatic valve 24 yields to permit the introduction of the outer guide sheath 16 through it, but otherwise conforms about the outer surface of the sheath 16, thereby maintaining a fluid tight seal.

Preferably, the guide sheath 16 includes a precurved distal tip region 26, like a conventional "pig tail" catheter. The precurved distal tip region 26 assists in steering the guide sheath 16 into position within the heart chamber 12.

The physician advances the probe 18 through the handle 28 of the outer sheath 16. The handle 28 includes a second conventional hemostatic valve 30 that yields to permit the introduction of the flexible body 32 of the mapping probe 18 through it. At the same time, the valve 30 conforms about the outer surface of the body 22 to maintain a fluid tight seal.

Further details of the deployment and use of the introducer 14 and guide sheath 16 to establish a pathway for the probe 18 are set forth in pending U.S. patent application Ser. No. 08/033,641, filed Mar. 16, 1993, entitled "Systems and Methods Using Guide Sheaths for Introducing, Deploying, and Stabilizing Cardiac Mapping and Ablation Probes."

II. THE TISSUE EXAMINATION PROBE

As FIGS. 1 and 3 best show, the probe 18 has a handle 34 attached to the proximal end of the flexible catheter body 32. The distal end of the catheter body 32 carries a three dimensional structure 36. In FIGS. 1 and 3, the structure 36 takes the form of a basket. It should be appreciated that other three dimensional structures could be used.

The three dimensional basket structure 36 carries an array of electrodes 38.

As FIG. 1 shows, when deployed inside the heart chamber 12, the basket structure 36 holds the electrodes 38 in intimate contact against the endocardial surface of the heart chamber 12.

The catheter body 32 passes through the outer guide sheath 16. The sheath 16 has an inner diameter that is greater than the outer diameter of the catheter body 32. As a result, the sheath 16 can slide along the catheter body 32. The sheath handle 28 helps the user slide the sheath 16 along the catheter body 32.

As FIG. 2 shows, forward movement of the sheath handle 28 (i.e., toward the introducer 14) advances the distal end of the slidable sheath 16 upon the basket structure 36. In this position, the slidable sheath 16 captures and collapses the basket structure 36, entirely enclosing the basket structure 36.

As FIG. 1 shows, rearward movement of the sheath handle 28 (i.e., away from the introducer 14) retracts the slidable sheath 16 away from the basket structure 36. This removes the compression force, and the basket structure 36 opens to assume its prescribed three dimensional shape.

The probe 18 also preferably includes a sliding hemostat sheath 40. The physician slides the sheath 40 about the basket structure 36 to protect it during its advancement through the introducer 14. Once the basket structure 36 enters the guide sheath 16, the physician slides the hemostatic sheath 40 away rearward toward the probe handle 34. Further details of the use of the sheath 40 are disclosed in the above-identified pending Patent Application.

The basket structure 36 can itself be variously constructed. In the illustrated and preferred embodiment (see FIG. 3), the basket structure 36 comprises a base member 42 and an end cap 44. Generally flexible splines 46 extend in a circumferentially spaced relationship between the base member 42 and the end cap 44.

In the illustrated embodiment, eight, rectilinear splines 46 form the basket structure 36. However, additional or fewer splines 46 could be used, as could spline of different configurations.

In this arrangement, the splines 46 are preferably made of a resilient inert material, like Nitinol metal or silicone rubber. The splines 46 are connected between the base member 42 and the end cap 44 in a resilient, pretensed condition, shown in FIG. 3.

As FIG. 1 shows, the resilient splines 46 bend and conform to the endocardial tissue surface they contact. As FIG. 2 shows, the splines 46 also collapse into a closed, compact bundle in response to the external compression force of the sliding sheath 18.

Figure 4:
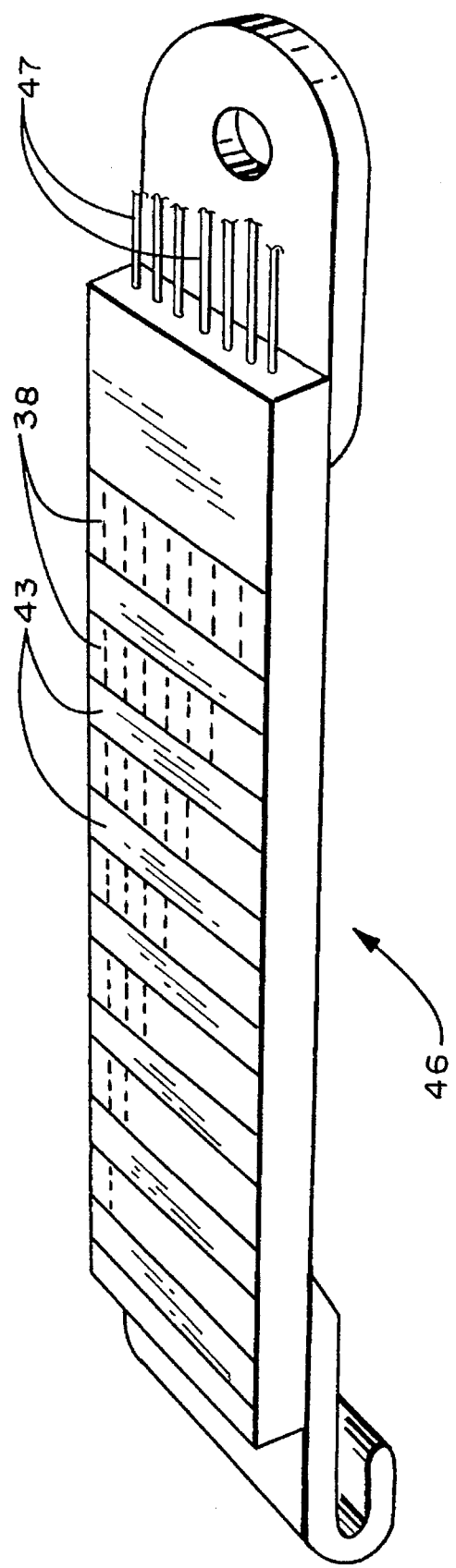
FIG. 4 is an enlarged perspective view of an electrode carrying spline associated with the probe shown in FIG. 1.

In the illustrated embodiment (see FIG. 4), each spline 46 carries eight electrodes 38. Of course, additional or fewer electrodes 38 can be used.

As will be described later, the system 10 can be operated in either a unipolar mode or a bipolar mode. The basket electrodes 38 can therefore be arranged in thirty-two bi-polar pairs, or as sixty-four uni-polar elements.

In the illustrated and preferred embodiment (as FIG. 4 best shows), the electrodes 38 are mounted to each spline 46 to maximize surface contact to endocardial tissue, while at the same time minimizing exposure to the surrounding blood pool. Incidental exposure of the electrodes 38 to blood while in contact with heart tissue introduces an unwanted artifact to E-Characteristic measurement, because the resistivity of blood is about three times lower than the resistivity of heart tissue. This artifact can skew the E-Characteristic measurement to a lower value, thereby reducing the desired contrast between healthy and infarcted tissue.

In the preferred embodiment (see FIG. 4), the electrodes 38 are made of platinum or gold plated stainless steel bands affixed to only one side of the splines 46. This is the side of the spline 46 that, in use, contacts endocardial tissue. The opposite surface of the splines 46 (which, in use, contacts the blood pool) is free of electrodes.

Figure 5:
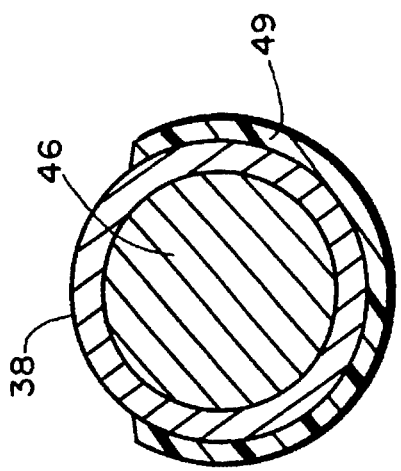
FIG. 5 is a cross sectional view of an alternative embodiment of an electrode that can be associated with the probe shown in FIG.1, taken generally along line 5—5 in FIG. 6.

In an alternative arrangement (see FIGS. 5 and 6), the electrodes 38 can take the form of rings that encircle the entire spline 46. In this arrangement, the rear side of the electrodes 38, which during use face the blood pool, are coated with an electrically insulating material 49 to prevent current transmission into blood.

It is believed that no more than 20% of the electrode surface should be exposed to the blood pool during use. Preferable, less than 5% of the electrode should be so exposed during use.

In an alternative arrangement (see FIGS. 6A to 6C), one or more of electrodes 38 can be introduced into the heart chamber through a vein or artery on a single flexible electrode support body 300, and not on a basket structure like that earlier described. The body 300 is illustrative of a family of flexible, elongated electrode supports of various alternative constructions. In the preferred and illustrated embodiment, the body 300 is about 1 to 2.5 mm in diameter and about 1 to 5 cm long.

Figure 27:
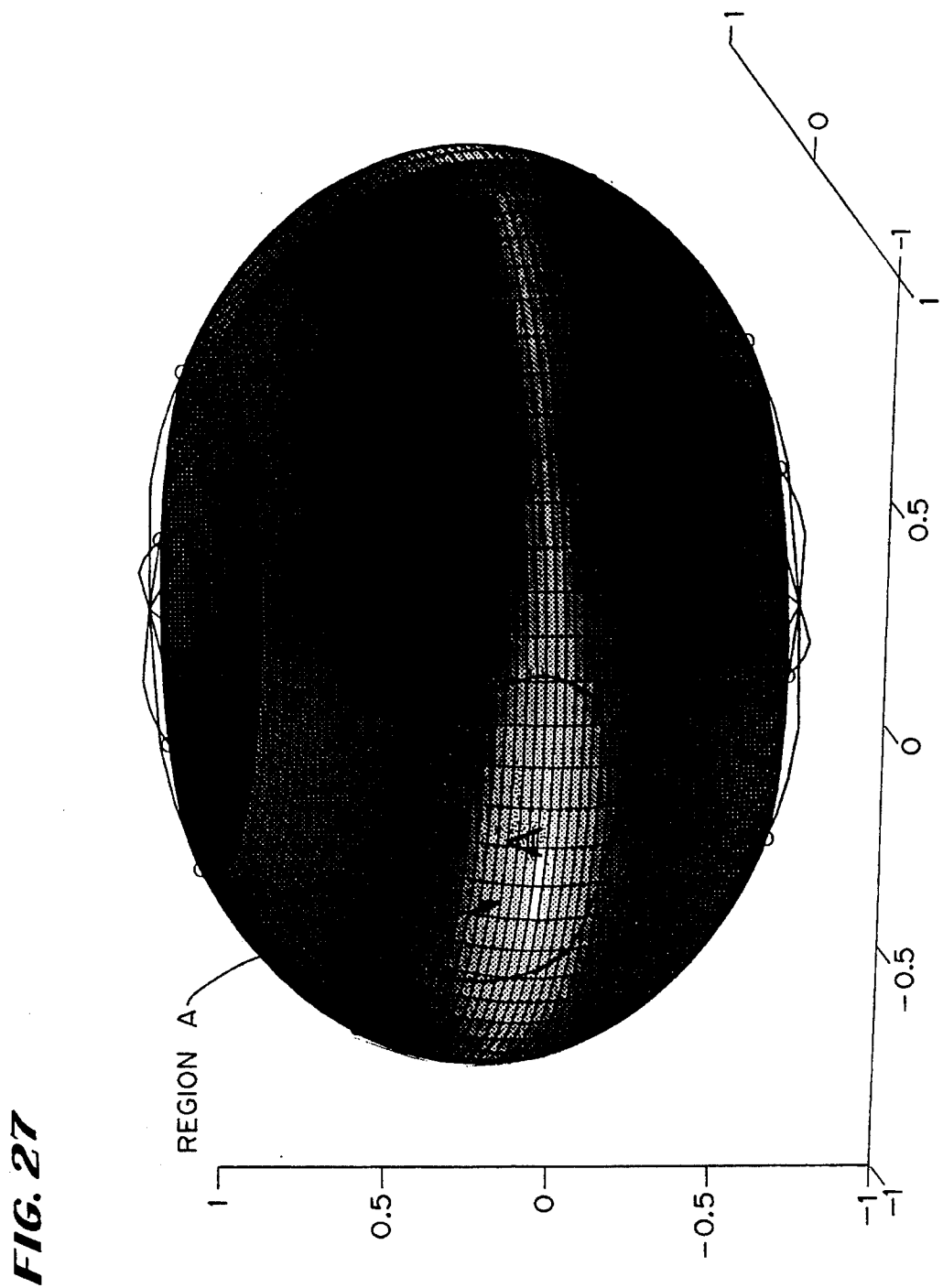
FIG. 27 is a representative display of the matched iso-E-Characteristics and iso-conduction information.

As FIG. 27 shows, the body 300 is carried at the distal end of a catheter tube 302 used to guide the body 300 into the heart. A handle 304 is attached to the proximal end of the catheter tube 302. The handle 304 and catheter tube 302 carry a steering mechanism 306 for selectively bending or flexing the support body 300 along its length, as the arrows in FIG. 6A show.

The steering mechanism 306 can vary. In the illustrated embodiment (see FIG. 6C), the steering mechanism 306 includes a rotating cam wheel 308 with an external steering lever 310 (as FIG. 6A shows). As FIG. 6C shows, the cam wheel 308 holds the proximal ends of right and left steering wires 312. The wires 312 pass through the catheter tube 302 and connect to the left and right sides of a resilient bendable wire or spring (not shown) within the ablating element support body 300.

As FIG. 6A shows, movement of the steering lever 310 flexes or curves the support body 300 from a generally straight configuration (shown in phantom lines in FIGS. 6A and 6B) into a generally arcuate curve (shown in solid lines in FIGS. 6A and 6B). Through flexing, the electrodes 38 can also be brought into conforming, intimate contact against the endocardial tissue, despite the particular contours and geometry that the wall presents.

As shown in FIG. 6B, the electrodes 38 comprise rings encircling the support body 300. In this arrangement, the rear sides of the electrodes 38, which, in use, face the blood pool, are preferably coated with the electrical insulating material 49 for the reasons stated above. Alternatively, the electrodes 38 can be affixed only to the tissue contacting side of the support body 300, thereby making the rear side of the support body 300 free of electrodes 38, like the rectilinear spline 46 shown in FIG. 4.

The electrodes 38 carried by the support body 300, as FIG. 6B shows, can by used in association with the process controller 20 to take one or more E-Characteristic measurements, just as the electrodes carried by the basket structure. The support body 300 can be moved sequentially to different endocardial sites to obtain a plurality of E-Characteristic measurements, which can be processed in the same manner as those taken by the stationary basket structure.

Further details of flexible electrode carrying elements can be found in copending U.S. patent application Ser. No. 08/138,142, filed Oct. 15, 1993, entitled "Systems and Methods for Creating Long, Thin Lesions in Body Tissue."

Figure 11:
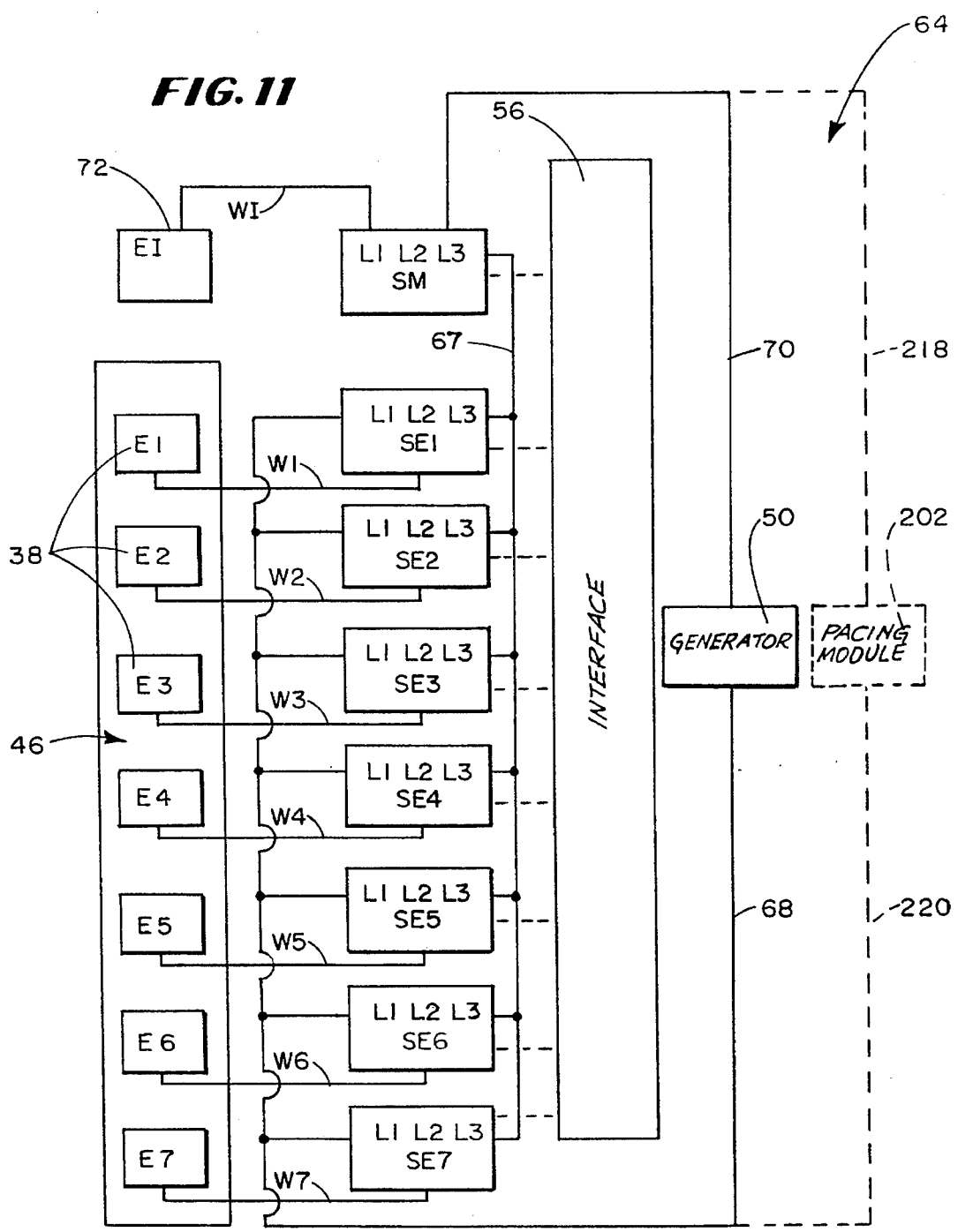
FIGS. 11 and 12 are schematic views of the details of the switching element shown in FIGS. 7 to 10.

In the illustrated embodiments (see FIGS. 4 and 6), a signal wire 47 made from a highly conductive metal, like copper, leads from each electrode 46 (these signal wires are also shown diagrammatically in FIG. 11). The signal wires 47 extend down the associated spline 46, by the base member 42, and into the catheter body 32. An inert plastic wrapping 43 preferably covers each spline 46 and electrode support body 300, except where the electrodes 38 project, to shield the signal wires.

The eight signal wires 47 for each spline 46 are twisted together to form a common bundle. The eight common bundles (not shown) are, in turn, passed through the catheter body 32 of the mapping probe 18. The common bundles enter the probe handle 34.

The sixty-four signal wires 47 are connected within the probe handle 34 to one or more external connectors 48, as FIG. 3 shows. In the illustrated embodiment, each connector contains thirty-two pins to service thirty-two signal wires.

In an alternative arrangement (not shown), the electrodes 38 can be connected to a multiplexer/demultiplexer (M/DMUX) block (not shown) to reduce the number of signal wires carried by the catheter body 32. The M/DMUX block can comprise a multi-die integrated circuit mounted on a flexible support and wrapped about the catheter body 32. The signal-to-noise-ratio is thereby improved.

III. MEASURING AND MAPPING THE TISSUE E-CHARACTERISTIC

The system 10 transmits electrical current in a selected manner through the basket electrodes 38 in contact with endocardial tissue. From this, the system 10 acquires impedance information about the heart tissue region that the basket electrodes 38 contact. The system 10 processes the impedance information to derive the E-Characteristic, which assists the physician in identifying regions of infarcted tissue where ablation therapy may be appropriate.

For these purposes (see FIG. 3), the system 10 includes the process controller 20. The process controller 20 includes a current generator module 50 and a signal processor module 52. The connectors 48 electrically couple the basket electrodes 38 to both the generator module 50 and the processor module 52.

A. The Current Generator Module

The generator module 50 conveys a prescribed current signal to individual basket electrodes 38.

Figure 7:
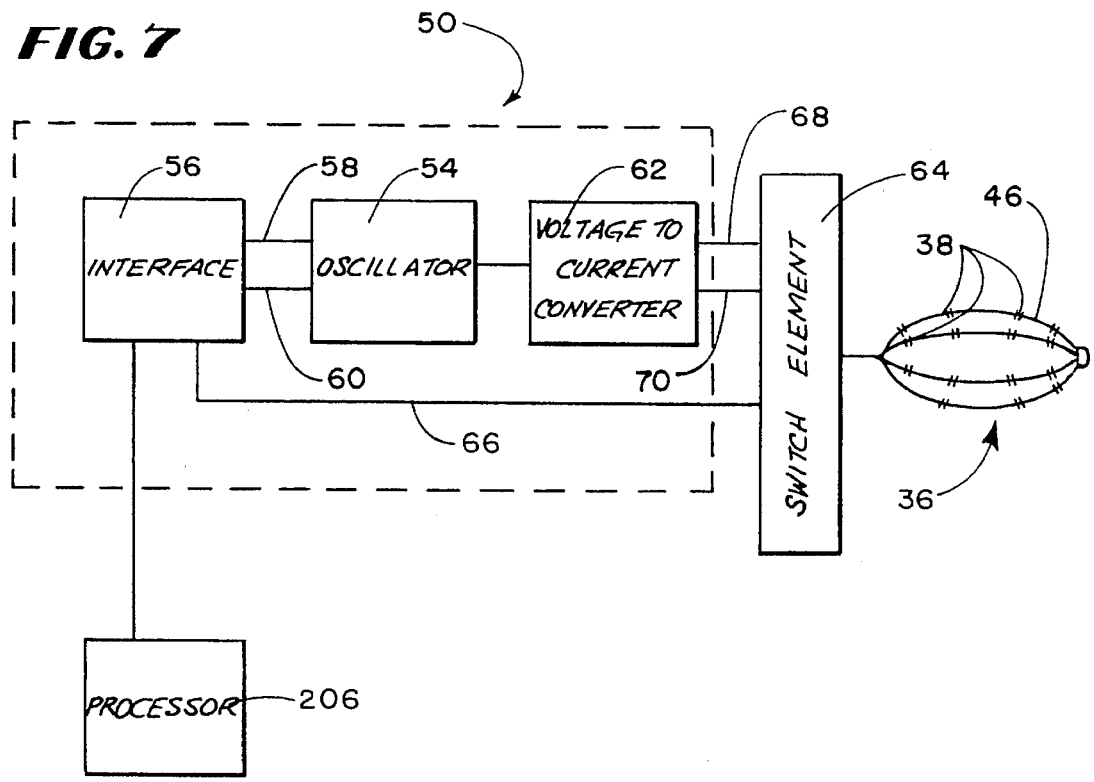
FIG. 7 is a schematic view of the current generator module and switching element of the process controller for the system shown in FIG. 1.

In the illustrated and preferred embodiment (see FIG. 7), the generator module 50 includes an oscillator 54 that generates a sinusoidal voltage signal. An associated interface 56 has a bus 58 that controls the frequency of the output voltage signal and a bus 60 that controls the amplitude of the output voltage signal. The interface 56, in turn, is programmed by a host processor 206, which will be described in greater detail later.

The oscillator 54 has as an output stage that includes a voltage-to-current converter 62. In conventional fashion, the converter 62 converts the sinusoidal voltage signal to current.

In the illustrated and preferred embodiment, the transmitted current has an amplitude of about 0.1 milliamps to 5.0 milliamps. The lower range of the current amplitude is selected to be high enough to overcome the influence of the double layer at the tissue-electrode interface on the E-Characteristic measurement. The high range of the current amplitude is selected to avoid the induction of fibrillation.

The current has a frequency in a range of about 5 to 50 kHz. The range is selected to avoid the induction of fibrillation, as well as provide contrast between infarcted tissue and healthy tissue. The output of the converter 62 can comprise a constant current with a constant frequency within the above range. Alternatively, the interface 56 can control the modulation of the frequency of the current signal within the prescribed range. Deriving tissue E-Characteristic by transmitting currents with different frequencies better differentiates among different tissue morphologies. It has been determined that lower frequencies within the range provide E-Characteristics yielding greater quantitative contrast between infarcted and healthy tissues than higher frequencies in this range.

The current output of the module 50 is supplied to the basket electrodes 38 via supply path 68 through a switching element 64. The interface 56 electronically configures the switching element 64 to direct current in succession to selected basket electrodes 38 through their associated signal wires in either a unipolar mode or a bipolar mode. Line 66 constitutes the control bus for the switching element 64.

Figure 8:
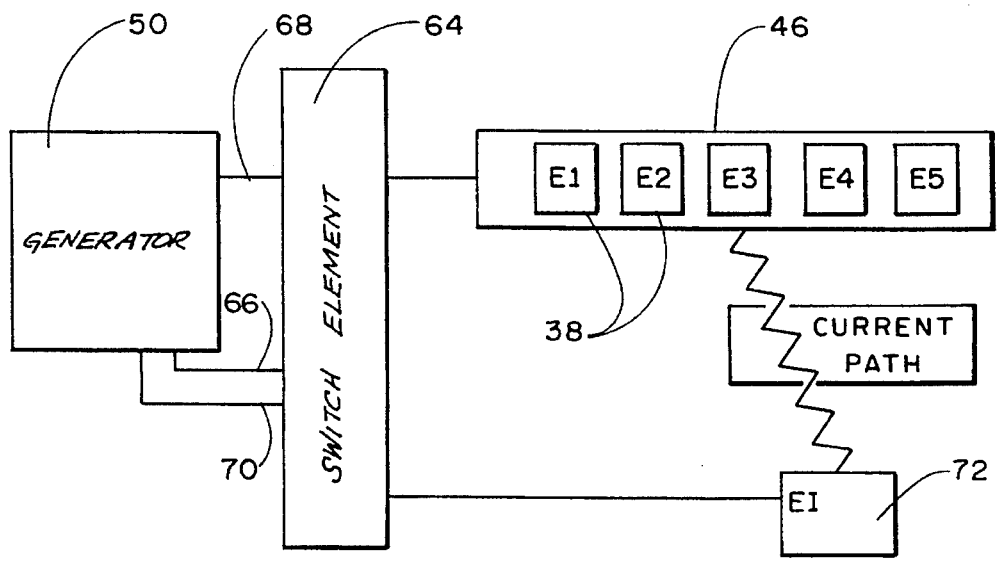
FIG. 8 is a diagrammatic view of the current generator module and switching element when operated in a Unipolar Mode.

As FIG. 8 shows, when operated in a unipolar mode, the current return path 70 to the generator module 50 is provided by an exterior indifferent electrode 72 attached to the patient.

Figure 9:
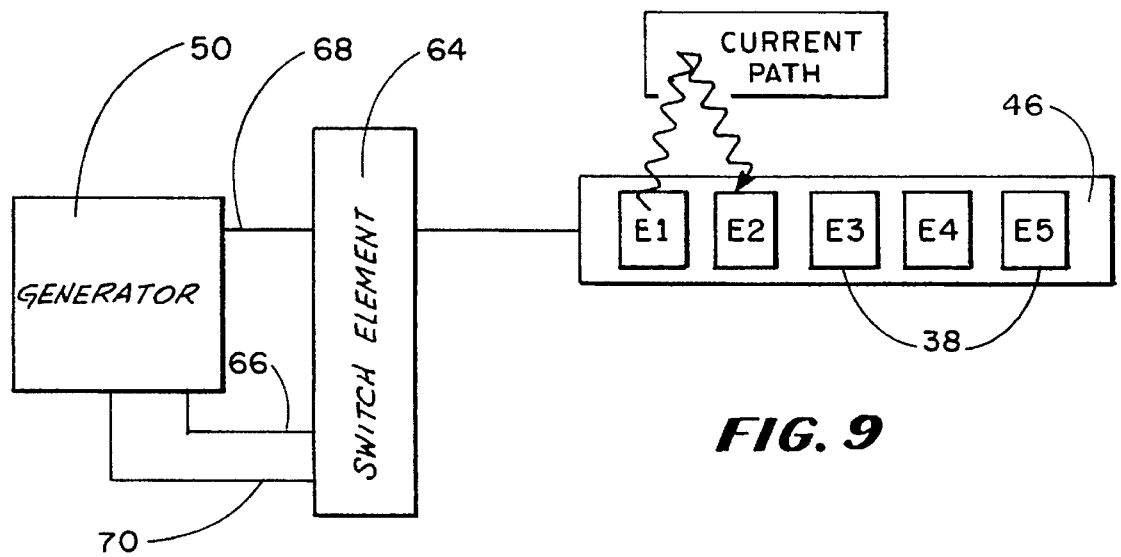
FIG. 9 is a diagrammatic view of the current generator module and switching element when operated in a Bipolar Two Electrode Mode.
Figure 10:
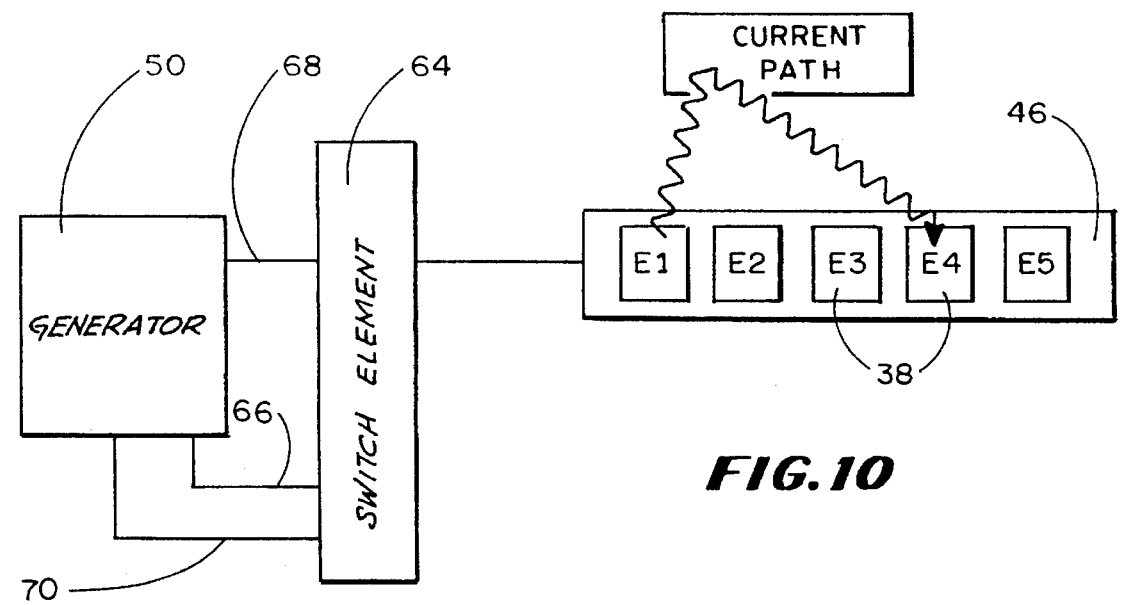
FIG. 10 is a diagrammatic view of the current generator module and switching element when operated in a Bipolar Four Electrode Mode.

When operated in a bipolar mode, the current return path 70 is provided by an electrode carried on the basket structure 36 itself. In the illustrated and preferred embodiment, the bipolar return electrode is either located immediately next to or three electrodes away from the selected transmitting basket electrode along the same spline. The first circumstance (shown in FIG. 9) will be called the Bipolar Two Electrode Mode. The second circumstance (shown in FIG. 10) will be called the Bipolar Four Electrode Mode.

The configuration of the switching element 64 can vary. FIG. 11 diagrammatically shows one preferred arrangement.

FIG. 11 shows for illustration purposes a spline 46 with seven adjacent electrodes 38, designated E1 to E7. Each electrode E1 to E7 is electrically coupled to its own signal wire, designated W1 to W7. The indifferent electrode, designated EI in FIG. 11, is also electrically coupled to its own signal wire WI.

In this arrangement, the switching element 64 includes an electronic switch $S_M$ and electronic switches $S_{E1}$ to $S_{E7}$ that electrically couple the current generator to the signal wires W1 to W7. The switch $S_M$ governs the overall operating mode of the electrodes E1 to E7 (i.e., unipolar or bipolar). The switches $S_{E1}$ to $S_{E7}$ govern the electrical conduction pattern of the electrodes E1 to E7.

The switches $S_M$ and $S_{E1\ to\ E7}$ are electrically coupled to the current source. The supply path 68 of the generator module 50 is electrically coupled to the leads L1 of the switches $S_{E1\ to\ E7}$. The return path 70 of the generator module 50 is electrically coupled to the center lead L2 of the mode selection switch $S_M$. A connector 67 electrically couples the leads L3 of the switches $S_M$ and $S_{E1\ to\ E7}$.

The center leads L2 of the selecting switches $S_{E1\ to\ E7}$ are directly electrically coupled to the signal wires W1 to W7 serving the electrodes E1 to E7, so that one switch $S_{E(N)}$ serves only one electrode $E_{(N)}$.

The lead L1 of the switch $S_M$ is directly electrically coupled to the signal wire WI serving the indifferent electrode EI.

Figure 12:
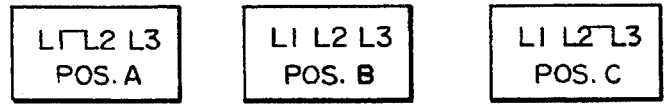

The interface 56 electronically sets the switches $S_M$ and $S_{E1\ to\ E7}$ among three positions, designated A, B, and C in FIG. 12.

As FIG. 12 shows, Position A electrically couples leads L1 and L2 of the associated switch. Position C electrically couples leads L2 and L3 of the associated switch. Position B electrically isolates both leads L1 and L3 from lead L2 of the associated switch.

Position B is an electrically OFF position. Positions A and B are electrically ON positions.

By setting switch $S_M$ in Position B, the interface 56 electronically inactivates the switching network 54.

By setting switch $S_M$ in Position A, the interface 56 electronically configures the switching element for operation in the unipolar mode. The center lead L2 of switch $S_M$ is coupled to lead L1, electronically coupling the indifferent electrode EI to the return of the current generator. This configures the indifferent electrode EI as a return path for current.

With switch $S_M$ set in Position A, the interface 56 electronically selectively configures each individual electrode E1 to E7 to emit current by sequentially setting the associated switch $S_{E1\ to\ E7}$ in Position A. When the selected electrode E1 to E7 is so configured, it is electronically coupled to the supply of the current generator and emits current. The indifferent electrode EI receives the current sequentially emitted by the selected electrode E1 to E7.

By setting switch $S_M$ in Position C, the interface 56 electronically isolates the indifferent electrode EI from the electrodes E1 to E7. This configures the switching element for operation in the bipolar mode.

With switch $S_M$ set in Position C, the interface 56 can electronically alter the polarity of adjacent electrodes E1 to E7, choosing among current source, current sink, or neither.

By setting the selected switch $S_{E1\ to\ E7}$ in Position A, the interface 56 electronically configures the associated electrode E1 to E7 to be a current source. By setting the selected switch $S_{E1\ to\ E7}$ in Position C, the interface 56 electronically configures the associated electrode E1 to E7 to be a current sink. By setting the selected switch $S_{E1\ to\ E7}$ in Position B, the interface 56 electronically turns off the associated electrode E1 to E7.

In the Bipolar Two Electrode Mode, the interface 56 first configures the electrode E1 to be a current source, while configuring the immediate adjacent electrode E2 to be a current sink, while turning off the remaining electrodes E3 to E7. After a preselected time period, the interface 56 then turns off electrode El, configures electrode E2 to be a current source, configures the next immediate adjacent electrode E3 to be a current sink, while keeping the remaining electrodes E4 to E7 turned off. After a preselected time period, the interface 56 then turns off electrode E2, configures electrode E3 to be a current source, configures the next immediate adjacent electrode E4 to be a current sink, while keeping the remaining electrodes E1 and E5 to E7 turned off. The interface 56 cycles in this timed sequence until electrodes E6 and E7 become the current source/sink bipolar pairs (the remaining electrodes E1 to E5 being turned off). The cycle can then be repeated, if desired, or ended after one iteration.

In the Bipolar Four Electrode Mode, the interface 56 first configures the electrode E1 to be a current source, while configuring the third adjacent electrode E4 to be a current sink, while turning off the remaining electrodes E2, E3, and E5 to E7. After a predetermined time period, the interface 56 turns off electrode El, configures electrode E2 to be a current source, configures the next third adjacent electrode E5 to be a current sink, while keeping the remaining electrodes E3, E4, E6, and E7 turned off. After a predetermined time period, the interface 56 turns off electrode E2, configures electrode E3 to be a current source, configures the next third adjacent electrode E6 to be a current sink, while keeping the remaining electrodes E1, E2, E4, E5, and E7 turned off. The interface 56 cycles in this timed sequence until electrodes E4 and E7 become the current source/sink bipolar pairs (the remaining electrodes E1 to E3, E5, and E6 being turned off. The cycle can then be repeated, if desired, or ended after one iteration.

In the preferred embodiment, there is a switching element 64 for the electrodes on each basket spline, with the interface 56 independently controlling each switching element.

B. Computing Tissue E-Characteristic

Figure 13:
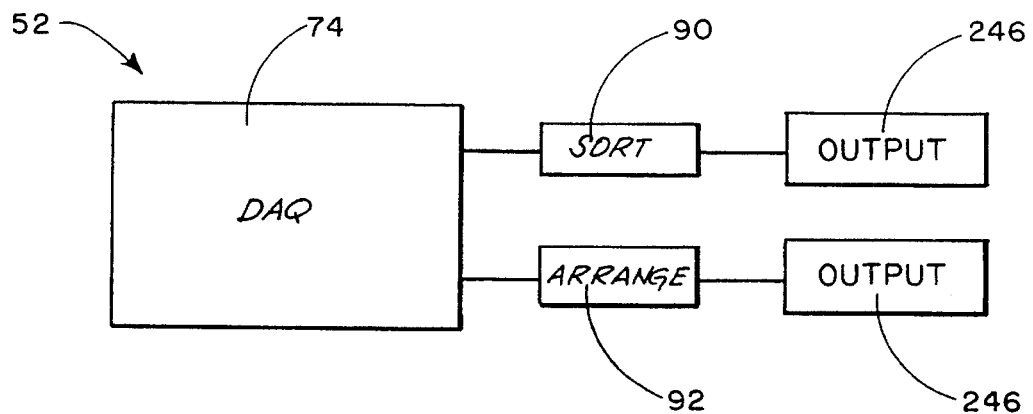
FIG. 13 is a schematic view of the signal processor module of the process controller for the system shown in FIG. 1.

As FIG. 13 shows, the signal processor module 52 includes a data acquisition system While current is emitting by a selected basket electrode, the system 74 senses the voltage in the tissue path using selected electrodes on the basket 36.

Based upon the data acquired by the system 74, the host processor 206 computes the E-Characteristic of the tissue path as follows:

(1) When operated in the Unipolar Mode, the E-Characteristic is the impedance of the tissue path computed based upon the following equation:

$$\text{Impedance(ohms)} = \frac{\text{PathVoltage(volts)}}{\text{PathCurrent(amps)}}$$

The PathVoltage and PathCurrent are both root mean squared (RMS) values.

In the unipolar mode (see FIG. 8), the voltage is measured between each transmitting electrode and the indifferent electrode (or between EI and $E_{(n)}$, where n represents the location of the current emitting electrode). The impedance computed by the host processor 206 in this mode reflects not only the impedance of the underlying myocardial tissue, but also includes the impedance of the other tissue mass in the path. The computed impedance in this mode therefore is not the actual impedance of the myocardial tissue itself. Rather, it provides a relative scale of impedance (or E-Characteristic) differences of the myocardial tissue lying in contact with the spline electrodes.

(2) When operated in the Bipolar Mode, the E-Characteristic of the tissue is the resistivity of the tissue path, computed as follows:

$$\text{Resistivity(ohm} \cdot \text{cm)} = \text{Impdedance(ohm)} \times k\text{(cm)}$$

$$\text{Impedance(ohms)} = \frac{\text{PathVoltage(volts)}}{\text{PathCurrent(amps)}}$$

where k is a dimensional constant (in cm) whose value takes into account the methodology employed (i.e. either Bipolar Two Electrode Mode or Bipolar Four Electrode Mode) and the geometry of the electrode array (i.e., the size and spacing of the electrodes).

In general, k is approximately equal to the average cross sectional area of the current path divided by the distance between the voltage sensing electrodes. The accuracy of the k value can be further improved, if desired, empirically or by modeling.

The PathVoltage and PathCurrent are both root mean squared (RMS) values.

When operated in the Bipolar Two Electrode Mode (see FIG. 9), the voltage is measured between the two adjacent current emitting/receiving electrodes (or between E(n) and E(n+1). When operated in the Bipolar Four Electrode Mode (see FIG. 10), the voltage is measured between the two adjacent electrodes lying in between the current transmitting electrode and the third adjacent return path electrode (or between E(n+1) and E(n+2).

In either Bipolar Mode, the resistivity computed by the processor 206 reflects the actual resistivity of the myocardial tissue lying in contact with the spline electrodes. However, the Bipolar Two Electrode Mode is more prone to electric artifacts than the Bipolar Four Electrode Mode, such as those due to poor electrical contact between electrode and tissue.

Figure 14:
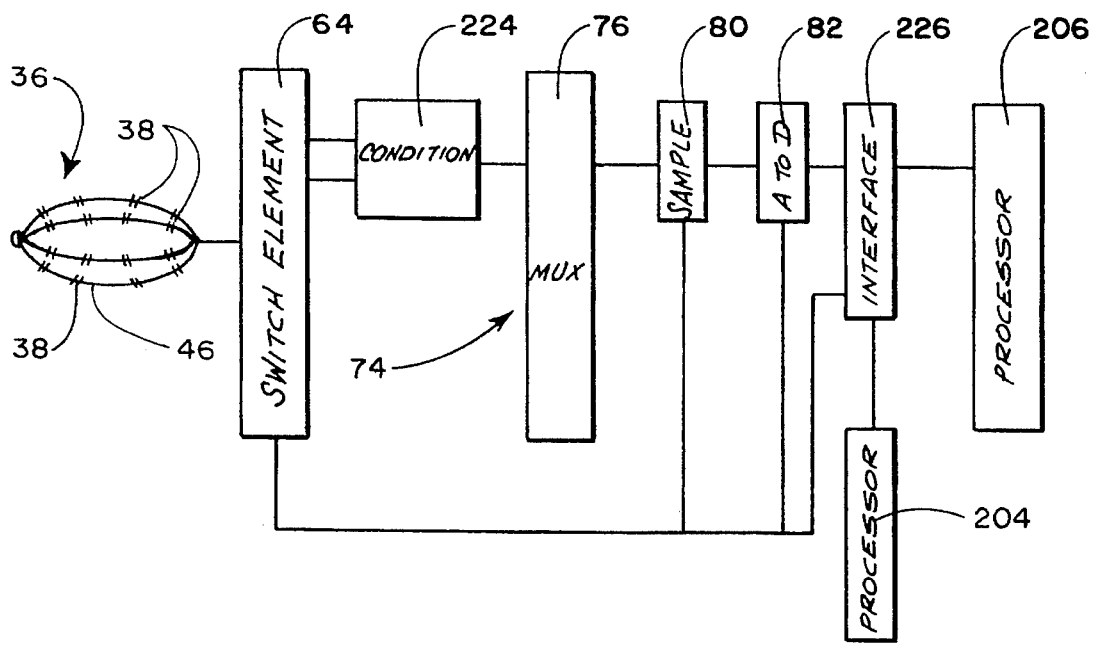
FIG. 14 is a schematic view of the E-Characteristic computing system of the signal processor module shown in FIG. 13.

As FIG. 14 shows, the voltage signals sensed by the basket electrodes 38 are passed back through the switching element 64 to the data acquisition system 74. As FIG. 11 shows, a signal conditioning element 224 preferably corrects alterations to the signal-to-noise ratio occurring in the voltage signals during propagation through the probe body 32.

The data acquisition system 74 includes a multiplexer 76 that selects and samples in succession the voltage associated with each transmitting electrode E(n) carried by the basket structure 36. For each selected current transmitting electrode E(n), the multiplexer 76 samples for a prescribed time period the analog sinusoidal voltage measured between the sensing electrodes.

A sample and hold element 80 stores the sampled analog voltage signals. The stored signals are sent to an analog-to-digital (A-to-D) converter 82, which converts the sampled voltage signals to digital signals. The multiplexer 76 makes possible the use of a single analog-to-digital conversion path.

The digital signals are sent to a host processor 206 through an interface 226. The host processor 206, based upon a conventional sorting scheme, obtains the peak voltage and, from that, computes the RMS voltage. The host processor 206 then computes the E-Characteristic, using the RMS voltage and RMS current (and, for the Bipolar Mode, the constant k) as described above. The RMS current is known by the processor 206, since it has been programmed by it through the interface 56 (see FIG. 7).

C. Processing the E-Characteristic

The computed E-Characteristic values can be processed by the system 10 in various ways.

In one embodiment (see FIG. 13), the signal processor module includes means 90 for sorting the multiple computed E-Characteristic values in absolute terms, arranging them according to a preassigned electrode numbering sequence, representing relative electrode position.

The means 90 can create as an output a table (either as a graphic display or in printed form), as follows:

TABLE 1

| SPLINE | ELECTRODE | E-CHAR |
|---|---|---|
| S1 | E1 | 75 |
| S1 | E2 | 114 |
| S1 | E3 | 68 |
| S1 | E4 | 81 |
| S2 | E1 | 69 |
| S2 | E2 | 71 |
| S2 | E3 | 67 |
| S2 | E4 | 66 |
| S3 | E1 | 123 |
| S3 | E2 | 147 |
| S3 | E3 | 148 |
| S3 | E4 | 140 |
| ... etc ... | ... etc ... | ... etc ... |

In Table 1, the spline elements of the basket are identified as S1, S2, S3, etc. The electrodes carried by each spline element are numbered from the distal end as El, E2, E3, and so on. The E-Characteristic values are expressed in terms of resistivity (ohm.cm). The values expressed are idealized and given for illustration purposes. In addition, or alternatively, the means 90 can also create as an output a two or three dimensional display that spatially maps the relative position of the computed absolute resistivity values, based upon basket electrode positions.

Figure 15:
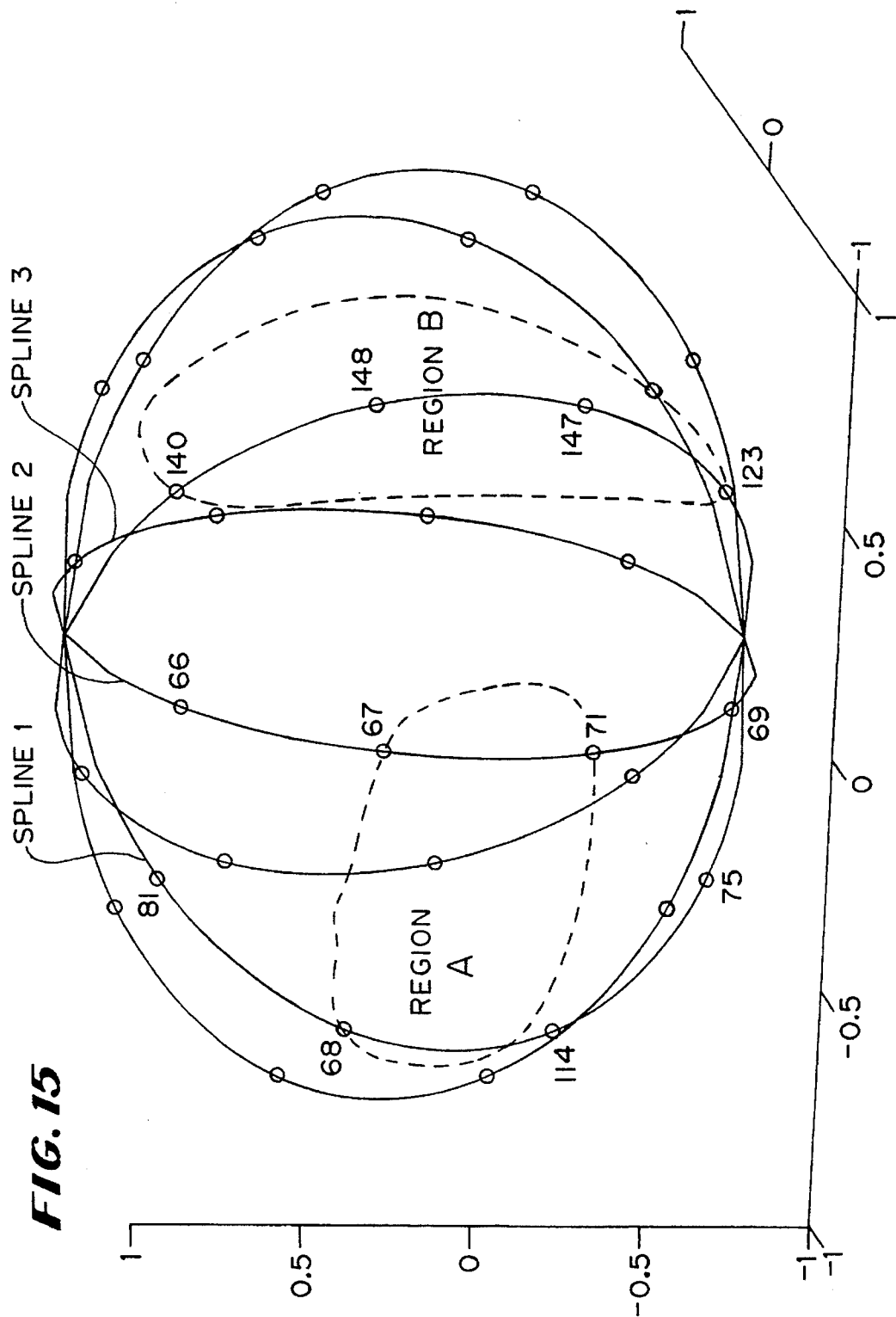
FIG. 15 is an illustrative, idealized display of the absolute tissue E-Characteristic values derived by the system shown in FIG. 14 arranged in spatial relation to a region of the heart.

FIG. 15 shows a representative display of E-Characteristics (expressed as resistivity values), based upon the data listed in Table 1. In FIG. 15, circled Area A identifies a region of low relative tissue resistivity, indicative of infarcted heart tissue. Area B in FIG. 15 is a region of normal tissue resistivity, indicative of healthy heart tissue.

Preferably, the signal processor module 52 also includes means 92 (see FIG. 13).for arranging the derived absolute E-Characteristics into groups of equal E-Characteristic values for display in spatial relation to the location of the electrodes 38. This output better aids the physician in interpreting the E-Characteristics, to identify the regions of low relative tissue E-Characteristics, where ablation may be appropriate.

Figure 16:
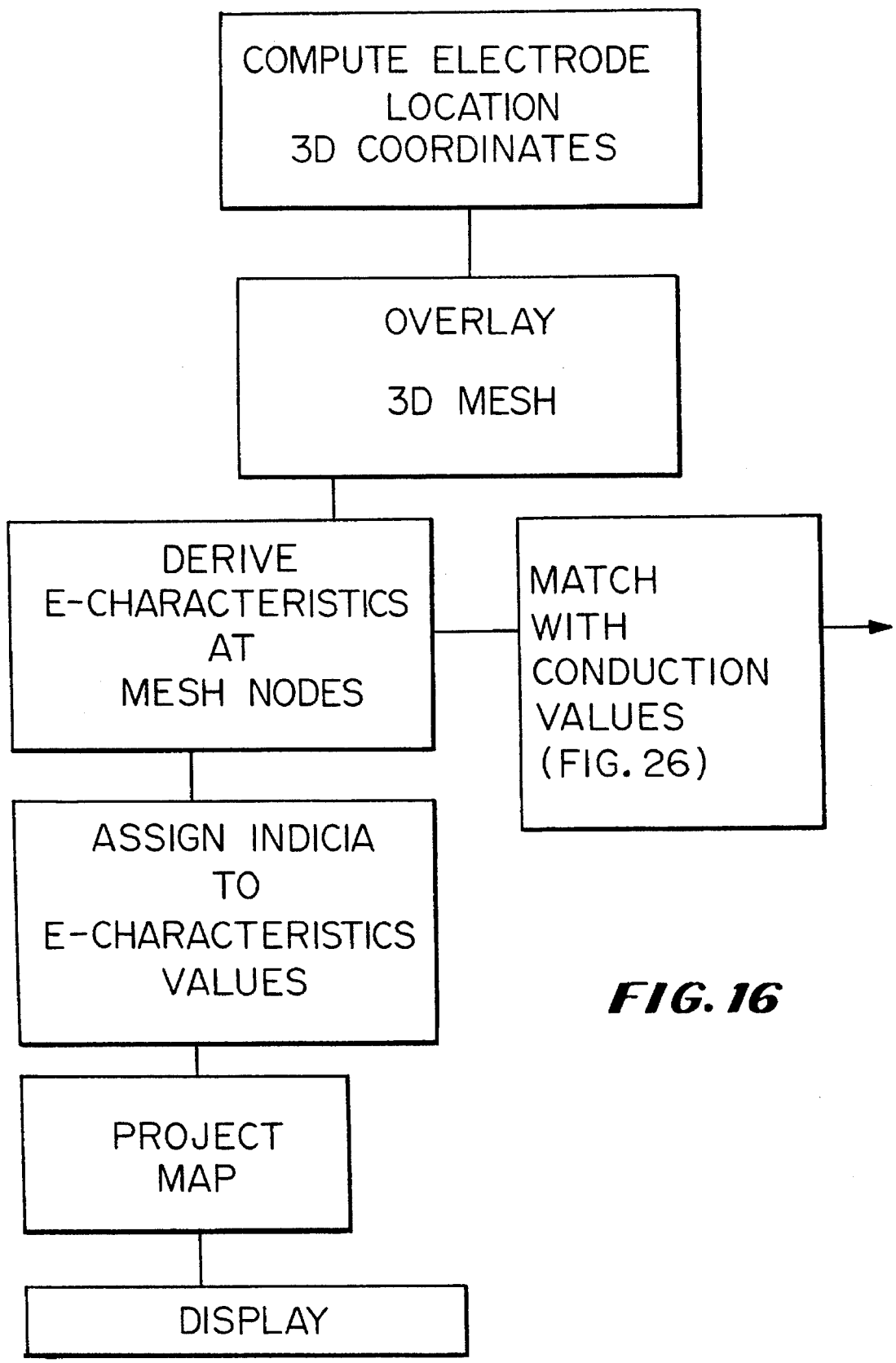
FIG. 16 is a flow chart showing the operation of the system that arranges the derived absolute tissue E-Characteristic values into groups of equal values.

As FIG. 16 shows, the means 92 includes a processing step that computes the location of the electrodes 38 in a three dimensional coordinate system. In the illustrated and preferred embodiment, a three dimensional spherical coordinate system is used.

The means 92 next includes a processing step that generates by computer a three dimensional mesh upon the basket surface. The points where the mesh intersect are called nodes. Some of the nodes will overlie the electrodes on the basket. These represent knots, for which the values of the E-Characteristic are known.

The values of the E-Characteristic for the remaining nodes of the three dimensional mesh have not been directly measured. Still, these values can be interpolated at each remaining node based upon the known values at each knot.

One method of doing this interpolation is using three dimensional cubic spline interpolation, although other methods can be used. The cubic spline interpolation process is incorporated in the MATLAB™ program, sold by The MathWorks Incorporated.

The means 92 creates an output display by assigning one distinguishing idicium to the maximum E-Characteristic value (whether actually measured or interpolated) and another distinguishing idicium to the minimum E-Characteristic value (again, whether actually measured or interpolated). In the illustrated and preferred embodiment, the distinguishing indicia are contrasting colors or shades.

The means 92 assigns computer generated intermediate indicia to intermediate measured and interpolated values, based upon a linear scale. In the illustrated and preferred embodiment, the intermediate indicia are color hues between the two contrasting colors or shades.

The means 92 projects the generated color (or selected indicia) map upon the basket surface, based upon location of the nodes in the three dimensional mesh. The means 92 thus creates as an output a display showing iso-E-Characteristic regions.

Figure 17:
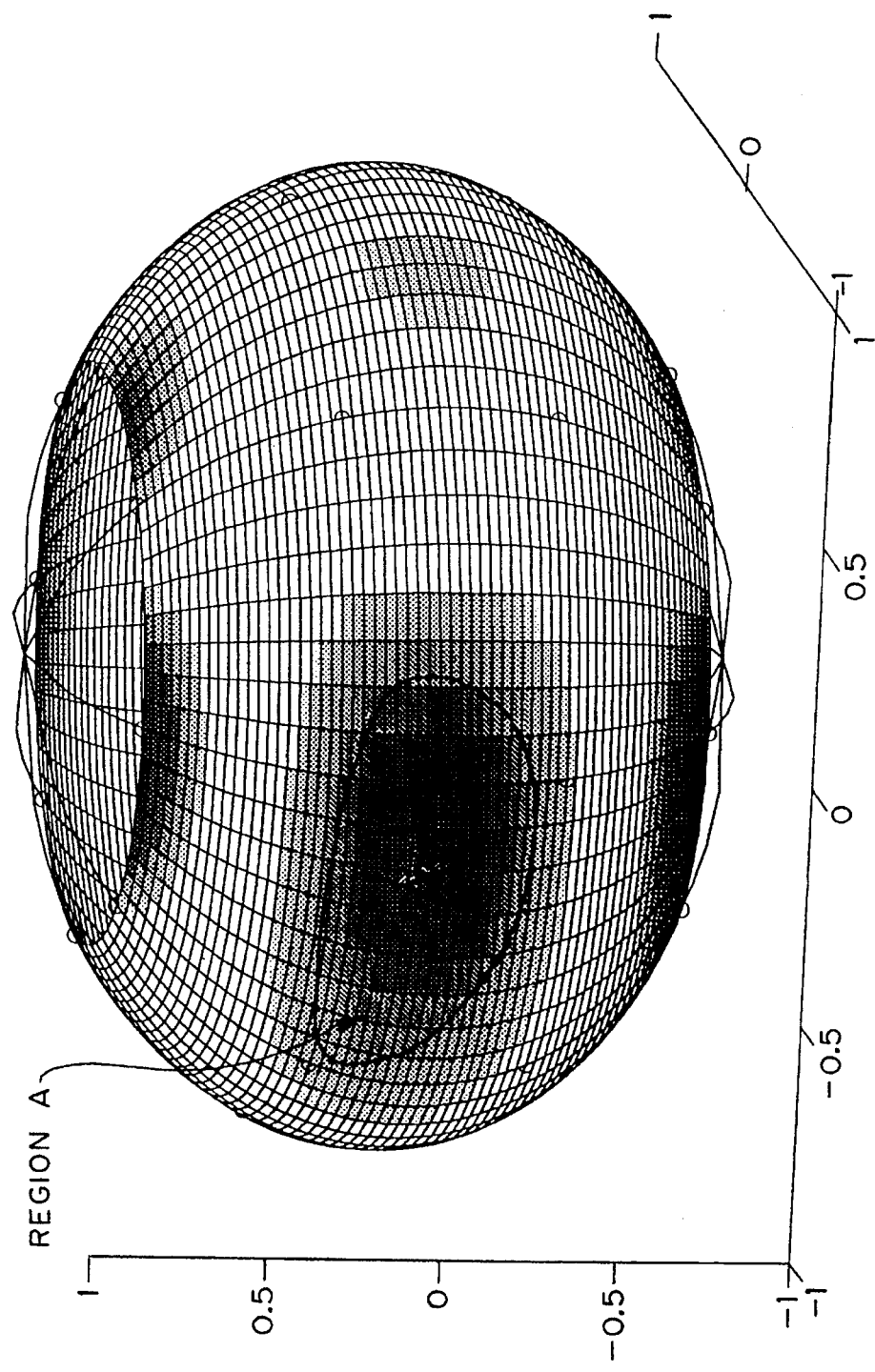
FIG. 17 is a representative display of the groups of equal E-Characteristic values derived by the system shown in FIG. 16 arranged in spatial relation to a region of the heart.

FIG. 17 shows a representative display of iso-resistivity regions, based upon the idealized, illustrative data listed in Table 1.

D. Matching E-Characteristic and Tissue Conductivity

Figure 18:
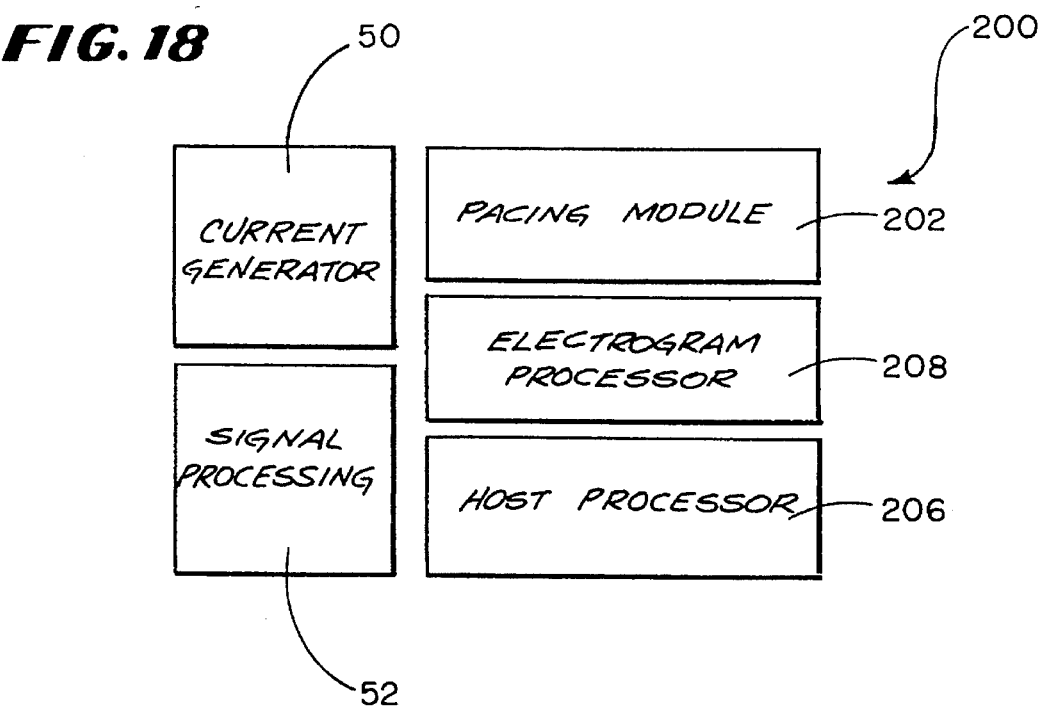
FIG. 18 is a diagrammatic view of an alternative embodiment of a controller that can be used in association with the system shown in FIG. 1.

FIG. 18 shows another embodiment of a process controller 200 that can be used in association with the probe 18, as already described.

The process controller 200 in FIG. 18, like the process controller 20 shown in FIG. 3, includes the current generator module 50 and the signal processing module 52 for deriving and processing tissue E-Characteristics in the manners previously discussed.

In addition, the process controller 200 in FIG. 18 includes a module 202 for pacing the heart to acquire electrograms in a conventional fashion. The pacing module 202 is electrically coupled to the probe connectors 48 to provide a pacing signal to one electrode 38, generating depolarization foci at selected sites within the heart. The basket electrodes 38 also serve to sense the resulting electrical events for the creation of electrograms.

Operation of the pacing module 202 is not required when ventricular tachycardia (VT) is either purposely induced (e.g., by programmed pacing) or occurs spontaneously. In this situation, the deployed basket electrodes 38 sense the electrical events associated with VT itself.

The process controller 200 in FIG. 18 further includes a second signal processing module 204 for processing the electrogram morphologies obtained from the basket electrodes 38.

The process controller 200 in FIG. 18 also includes a host processor 206 that receives input from the data acquisition system 74 and the electrogram processing module 204. The processor 206 analyzes the tissue E-Characteristic and electrogram information to compute a matched filtered output, which further enhances the CIR of ablation site identification.

The modules 202, 204, and 206 may be configured in various ways.

Figure 19:
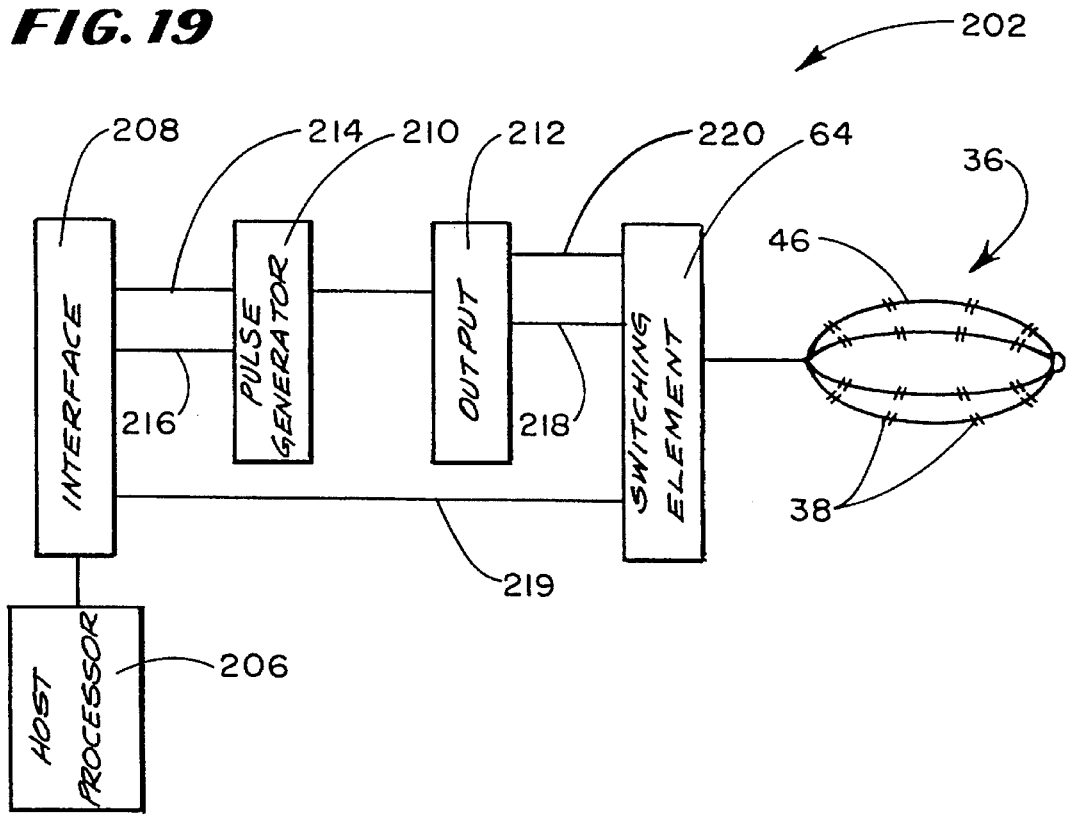
FIG. 19 is a diagrammatic view of the pacing module that the controller shown in FIG. 18 includes.

In the illustrated and preferred embodiment (see FIG. 19), the pacing module 202 includes a controller interface 208 coupled to the host processor 206, which will be described in greater detail later. The controller interface 208 is also coupled to pulse generator 210 and an output stage 212.

The output stage 212 is electrically coupled by supply path 220 and return path 218 to the same switching element 64 as the current generator module 50. The switching element 64 has been previously described and is shown schematically in FIG. 11. As FIG. 11 shows in phantom lines, the pacing module 202 and current generator module 50 are connected to the switching element 64.

The controller interface 208 includes control buses 214, 216, and 218. Bus 214 conveys pulse period control signals to the pulse generator 210. Bus 216 conveys pulse amplitude control signals to the pulse generator 210. Bus 219 constitutes the control bus path for the switching element 64.

When used to pace the heart, the switching element 64 distributes the signals generated by the pacing module 202 to selected basket electrodes 38. The pacing sequence is governed by the interface 208, which the host processor 206 controls.

The resulting electrogram signals sensed by the basket electrodes 38 are also passed back through the switching element 64 to the host processor 206 and the processing module 204 through the same analog processing path as the E-Characteristic signals, as FIG. 11 shows, and as already described.

Figure 20:
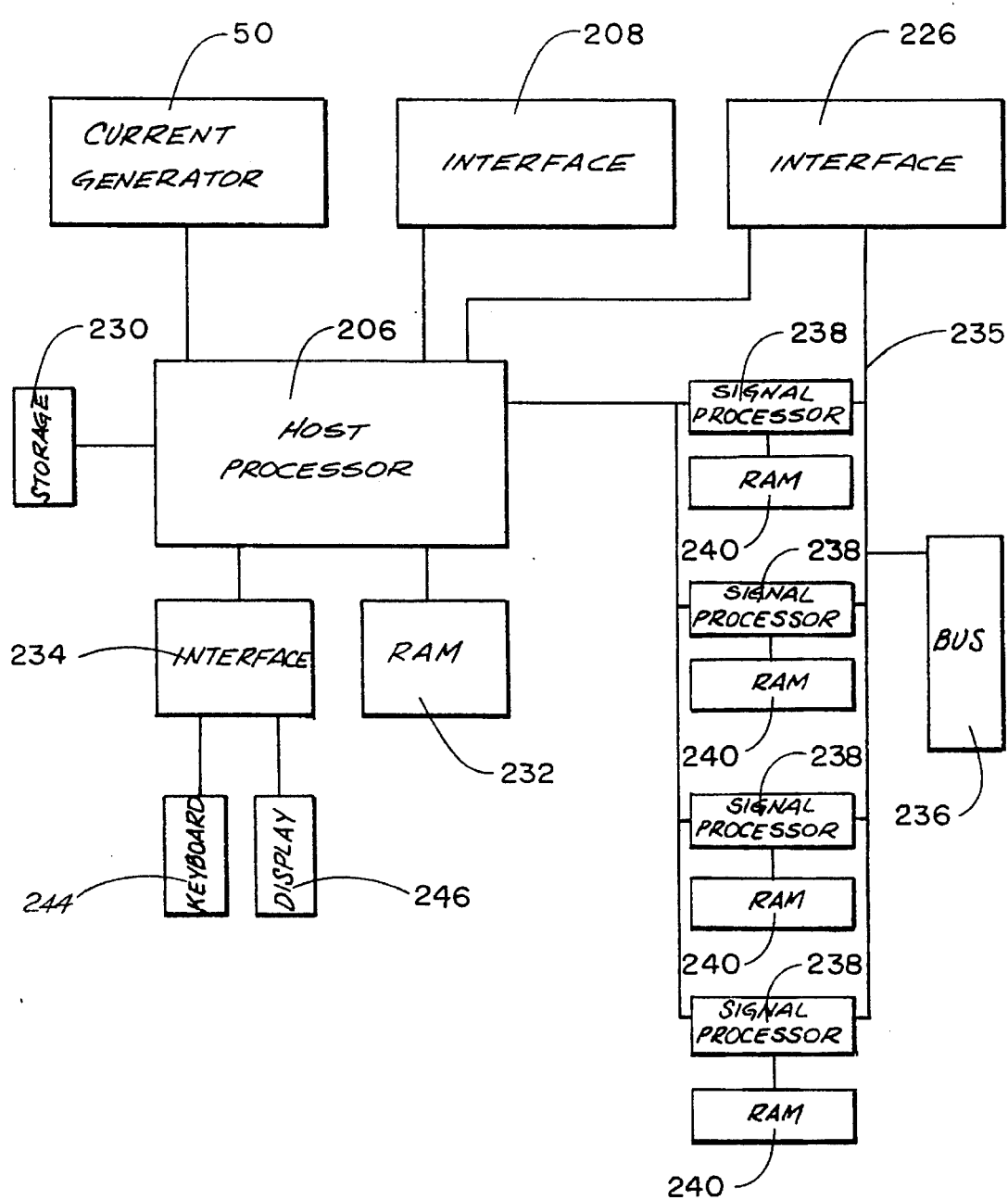
FIG. 20 is a diagrammatic view of the host processing unit and electrogram signal processing module with which the controller shown in FIG. 18 is associated.

FIG. 20 schematically shows the components of the host processor 206 and the electrogram processing module 204.

The host central processing unit (CPU) 206 communicates with a mass storage device 230 and an extended static RAM block 232. A user interactive interface 234 also communicates with the CPU 206.

As FIG. 20 shows, the interactive user interface 234 includes an input device 244 (for example, a key board or mouse) and an output display device 246 (for example, a graphics display monitor or CRT).

The CPU 206 also communicates with the 10 current generator module 50; pacing module 202 and the interface 226 for the system 74, as previously described. In this way, the CPU 206 coordinates overall control functions for the system 10.

As FIG. 206 shows, the electrogram processing module 204 includes a bus 235 and a bus arbiter 236 that receive the digital output of the A-to-D converter 82 through the interface 226. The bus arbiter 236 arbitrates the distribution of the digital electrogram morphology signals to one or more digital signal processors 238, which also form a part of the processing module 204 and which also communicate with the CPU 206.

The illustrated and preferred embodiment employs four signal processors 238 operating concurrently, but different numbers of processors 238 can be used. If N is the total number of basket electrodes and M is the number of processors 238, then each processor 238 is responsible for processing the signals coming from N/M electrodes in the Unipolar Mode and N/(2M) electrodes in the Bipolar Two or Four Mode.

To speed up data processing, each processor 238 includes a static RAM block 240. The data is processed real-time and stored in the blocks 240.

The signal processors 238 include various means for processing the electrogram signals as follows:

(i) to detect the earliest depolarization event;

(ii) to construct from the electrogram signals iso-chronal or iso-delay maps of the depolarization wavefronts, depending upon how the electrograms are obtained, which can be presented on the display device 246 for viewing by the physician; and (iii) to construct from the electrogram signals iso-conduction maps, which can also be presented on the display device 246 for viewing by the physician.

The CPU 206 employs additional means for processing the electrogram signals and the E-Characteristic signals as follows:

(iv) to match the iso-conduction maps with the iso-E-Characteristic maps, which can be presented on the display device 246 for viewing by the physician; and (v) based upon the matched output of (iv), to identify a potential ablation site.

(i) Identifying the Earliest Depolarization Event

Figure 21A:
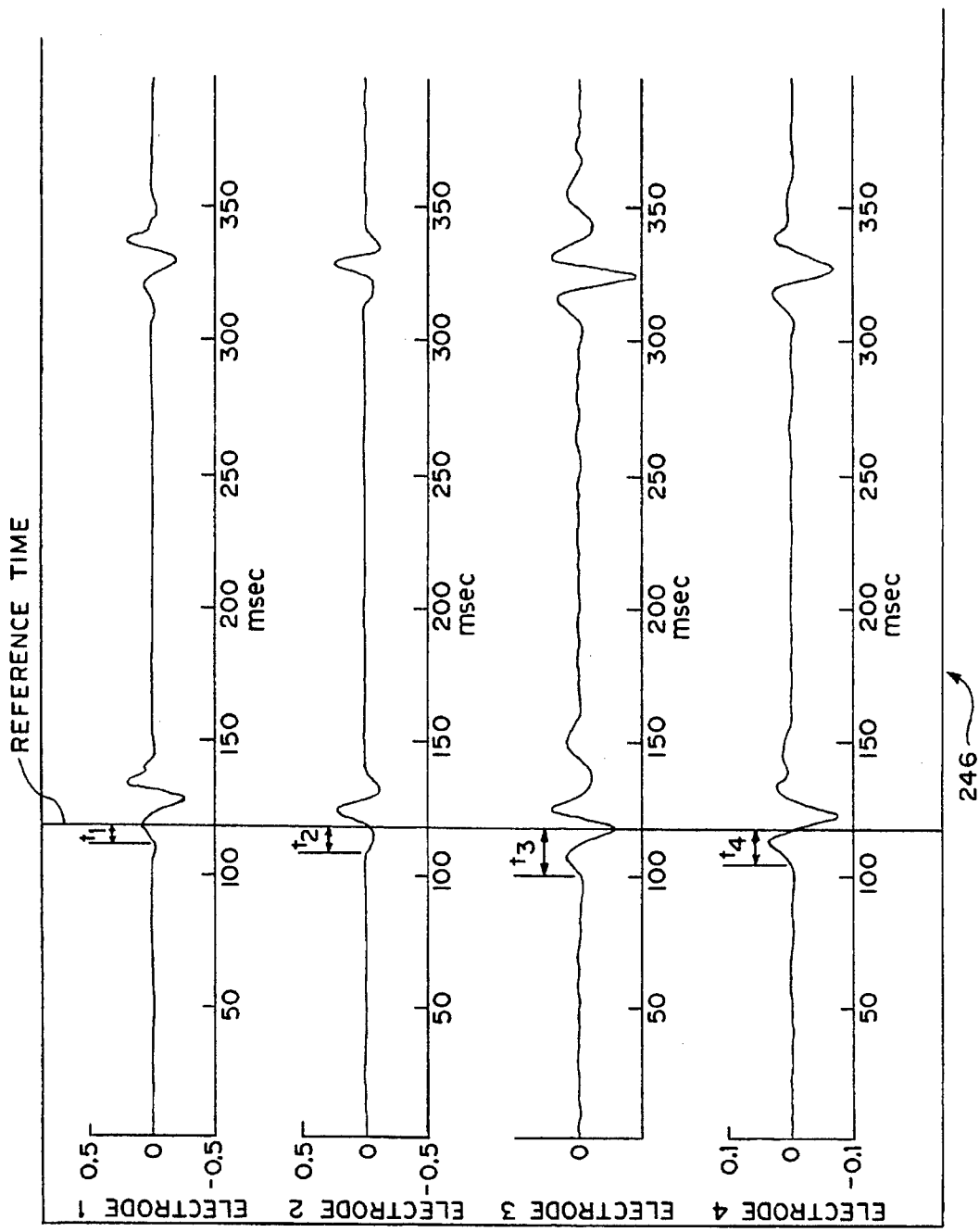
FIG. 21A is a view of four representative electrograms that can be used to compute electrogram events.
Figure 21B:
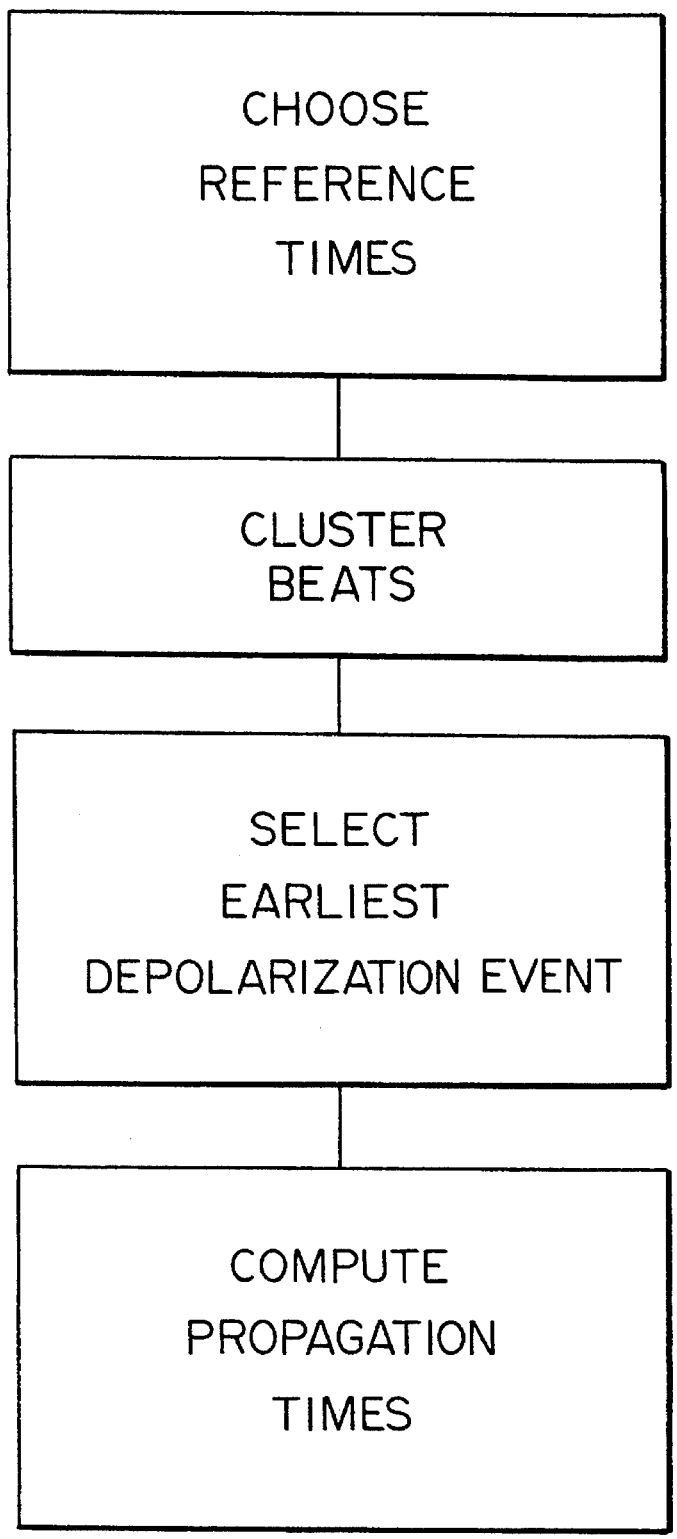
FIG. 21B is a flow chart showing the methodology for computing an electrogram event for processing by the controller shown in FIG. 18.

FIG. 21B shows the means 250 for detecting the early depolarization event.

The CPU 206 displays the electrograms on the display 246 of the interactive user interface 234 (see FIG. 21A). After analyzing the display 246, the physician can manually choose a reference time for conventional electrogram beat clustering purposes. The physician can use the mouse or a keyboard device 244 for this purpose.

In the situation where ventricular tachycardia is purposely induced or is occurring spontaneously, the electrogram beats are clustered relative to the reference time to compute the propagation time when an electrogram for ventricular tachycardia is sensed by each electrode 38. For all the beats in the selected cluster, the physician manually selects the earliest depolarization event for each electrode 38. The interactive interface 234 transmits the physician's choice to the host CPU 206, which creates a matrix of the computed propagation times.

In the situation where the heart is being paced by the module 202, the beats are clustered relative to the reference time for computing the activation delay for each electrogram. The activation delay is measured between the pacing pulse and the earliest depolarization event. For all the beats in the selected cluster, the physician manually selects the earliest depolarization event for each electrode 38. In this situation as before, the interactive interface 234 transmits the physician's choice to the host CPU 206, which creates a matrix of the computed activation delays.

FIG. 21A shows four representative electrograms of a heart undergoing VT. FIG. 21A shows the reference time selected for beat clustering purposes and the early depolarization events selected for the purpose of illustration. From this, the propagation times $t_1$; $t_2$; $t_3$; $t_4$ can be computed as the differences between the time of the depolarization event and the reference time in each electrogram.

(ii) Constructing an Iso-Chronal or Iso-Delay Displays

Figure 22:
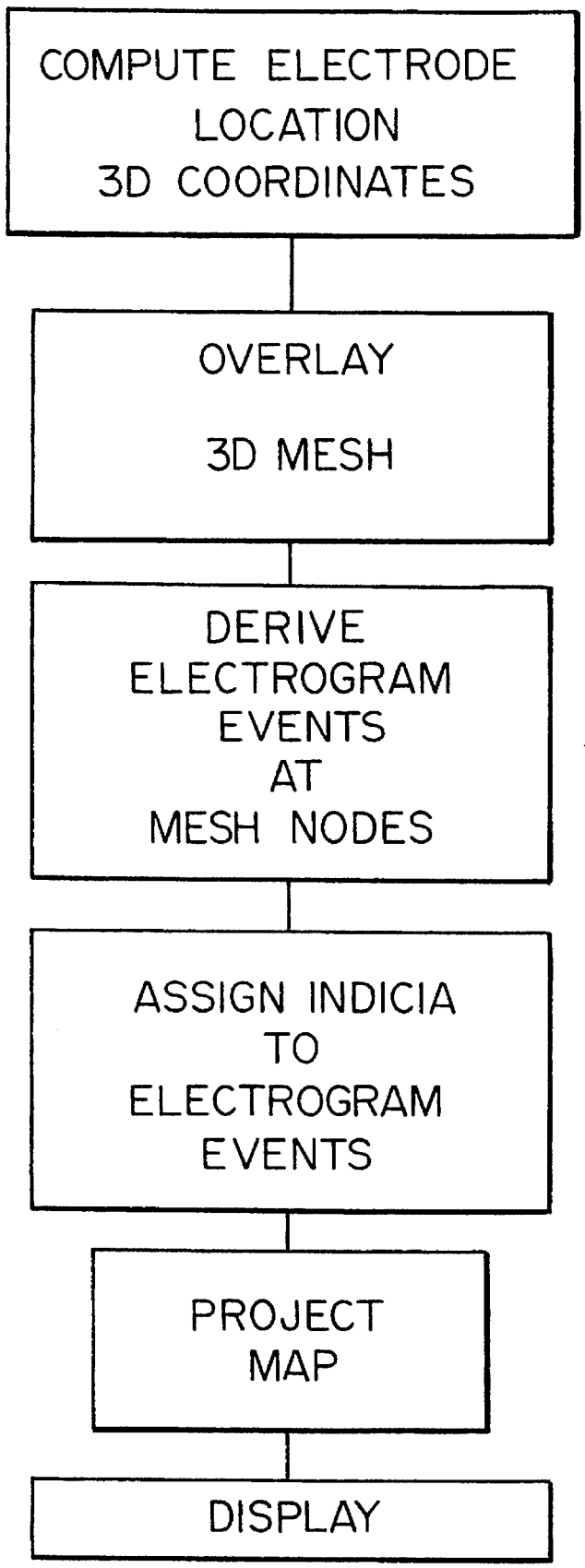
FIG. 22 is a flow chart showing the operation of the means for constructing an iso-display of the computed electrogram event.

FIG. 22 shows the means 252 for creating either an iso-chronal display of the propagation times (when VT is induced or spontaneously occurs) or an iso-delay display of activation times (when the module 202 is used to pace the heart). For purposes of description, each will be called the "computed electrogram event."

The means 252 generally follows the same processing steps as the means 92 (see FIG. 16) for creating the iso-E-Characteristic display.

The means 252 includes a processing step that computes the location of the electrodes in a spherical coordinate system.

The means 252 next generates by computer a three dimensional mesh upon the basket surface. The points where the mesh intersect are called nodes. Some of the nodes overlie the electrodes on the basket. These represent knots, for which the values of the computed electrogram event are known.

The values of the computed electrogram event for the remaining nodes of the three dimensional mesh have not been directly measured. Still, these values can be interpolated at each remaining node based upon the known values at each knot.

As before, three dimensional cubic spline interpolation can be used, although other methods can be used.

The means 252 creates an output display on the device 246 by assigning one color the maximum value of the computed electrogram event (whether actually measured or interpolated) and another color to the minimum value of computed electrogram event (again, whether actually measured or interpolated). Computer generated intermediate hues between the two colors are assigned by the host CPU 206 to intermediate measured and interpolated values, based upon a linear scale.

The means 252 projects the generated color map upon the basket surface, based upon location of the nodes in the three dimensional mesh.

Figure 23:
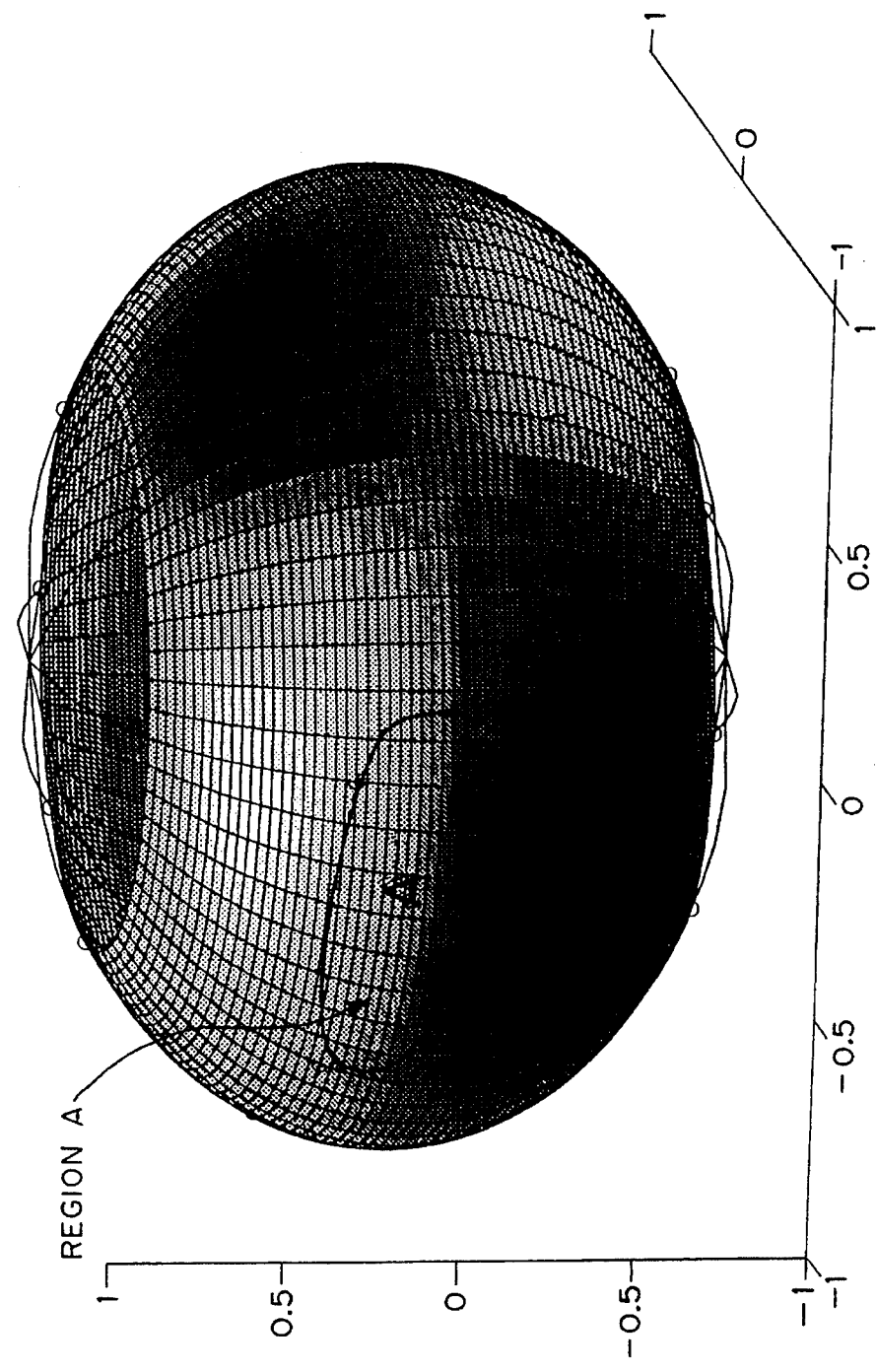
FIG. 23 is a representative iso-chronal display.

FIG. 23 shows a representative display generated according to this processing means. The CPU 206 generates this display on the display device 246 for viewing by the physician.

A potential ablation site can be identified at regions where a rapid transition of hues occurs. Area A on FIG. 23 shows such a region.

When the electrograms used for beat clustering show an induced or spontaneous VT, the resulting display is an iso-chronal map of the examined tissue region. When the electrograms used for beat clustering are based upon a paced heart, the display is an iso-delay map of the examined tissue region.

(iii) Creating Iso-Conduction

Figure 24:
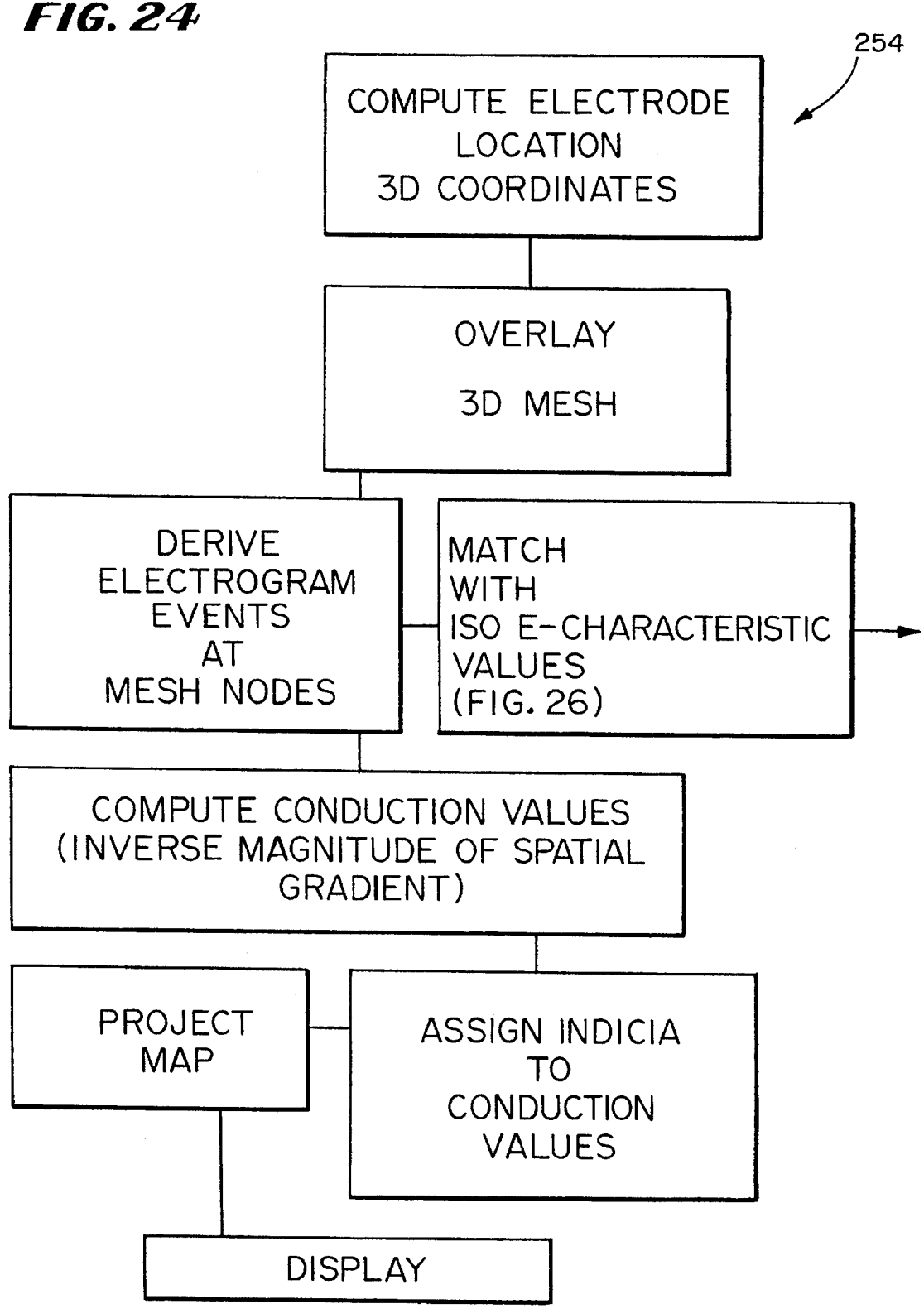
FIG. 24 is a flow chart showing the operation of the means for constructing an iso-conduction display of the computed electrogram event.

FIG. 24 shows the means 254 for creating an iso-conduction displays of the computed electrogram event.

An iso-conduction display more rapidly identifies the regions of slow conduction which are candidate ablation sites, than an iso-chronal or iso-delay display. The iso-conduction display requires less subjective interpretation by the physician, as the regions of slow conduction stand out in much greater contrast than on an iso-chronal or iso-delay display.

The means 254 draws upon the same input and follows much of the same processing steps as the means 252 just described. The means 254 computes the location of the electrodes in a spherical coordinate system and then generates a three dimensional mesh upon the basket surface. The means 254 interpolates the computed electrogram event for the nodes based upon the known values at the knots.

Unlike the previously described means 252, the means 254 computes the inverse of the magnitude of the spatial gradient of the computed electrogram event. This inverse spatial gradient represents the value of the conduction of the cardiac signal in the examined tissue.

To carry out this processing step, the means 254 first computes the spatial gradient computed electrogram event for each node of the mesh. The methodology for making this computation is well known.

Next, the means 254 computes the magnitude of the spatial gradient, using, for example, known three dimensional vector analysis. Then, the means 254 computes the inverse of the magnitude, which represents the conduction value.

The means 254 clips all magnitudes larger than a predetermined threshold value, making them equal to the threshold value. This processing step reduces the effects of inaccuracies that may arise during the mathematical approximation process.

The computation of conduction (i.e., the velocity of the propagation) can be exemplified for the case when propagation times are processed. By substituting the activation delays for propagation times, one can compute the conductions for data obtained from paced hearts.

Figure 25:
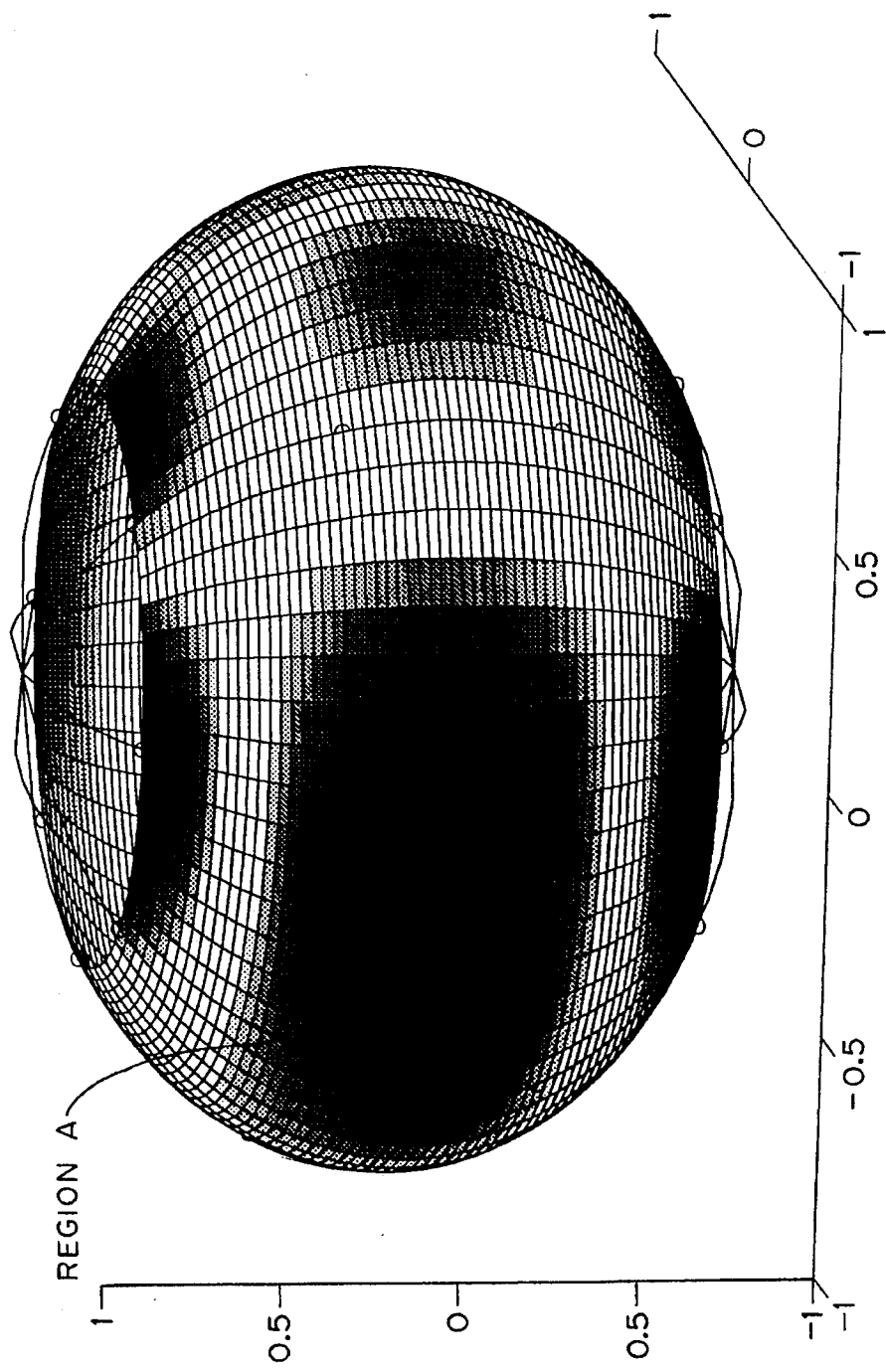
FIG. 25 is a representative iso-conduction display.

The location of any point on the three-dimensional mesh shown in FIG. 25 is given by the azimuth angle, $\phi$ and the elevation angle, $\delta$. The radius of the underlying surface is normalized to one. The conduction is defined by EQUATION (1):

EQUATION (1):

$$\text{Conduction}(\phi,\delta) = \left| \frac{d\text{space}}{d\text{Prop\_Time}(\phi,\delta)} \right|$$

Given that the radius of the meshed surface is one, one obtains the spatial gradient of propagation times:

EQUATION (2):

$$\frac{d\text{Prop\_Time}(\phi,\delta)}{d\text{space}} = \frac{\partial \text{Prop\_Time}(\phi,\delta)}{\partial \phi} \times \Phi + \frac{\partial \text{Prop\_Time}(\phi,\delta)}{\partial \delta} \times \Delta$$

where $\Phi$ and $\Delta$ are unity vectors of the spherical coordinate system defining the directions of the azimuth and elevation, respectively.

Thus, the conduction can be computed using EQUATION (3):

EQUATION (3):

$$\text{Conduction}(\phi,\delta) = \frac{1}{\sqrt{\left(\frac{\partial \text{Prop\_Time}(\phi,\delta)}{\partial \phi}\right)^2 + \left(\frac{\partial \text{Prop\_Time}(\phi,\delta)}{\partial \delta}\right)^2}}$$

which is actually the inverse of the spatial gradient magnitude. When the conduction is numerically approximated, the derivatives in EQUATION (3) can be computed by any numerical method appropriate for the estimation of first derivatives.

The means 254 creates a display by assigning one color the threshold conduction value (i.e., the maximum permitted value) and another color to the minimum conduction value. Computer generated hues are assigned to intermediate values, based upon a linear scale, as above described.

The means 254 projects the generated color map upon the basket surface, based upon location of the nodes in the three dimensional mesh.

FIG. 25 shows a representative iso-conduction display generated according to the just described methodology and using the same data as the iso-chronal display shown in FIG. 23. The CPU 206 generates this display on the display device 246 for viewing by the physician.

Area A in FIG. 25 shows a region of slow conduction, which appears generally at the same location as the rapid hue transition in FIG. 23 (also identified as Area A). FIG. 25 shows the more pronounced contrast of the region that the iso-conduction display provides, when compared to the iso-chronal display of FIG. 23. Thus, the iso-conduction display leads to a more certain identification of a potential ablation site.

(iv) Matching Iso-Conduction with Iso-E-Characteristic

Figure 26:
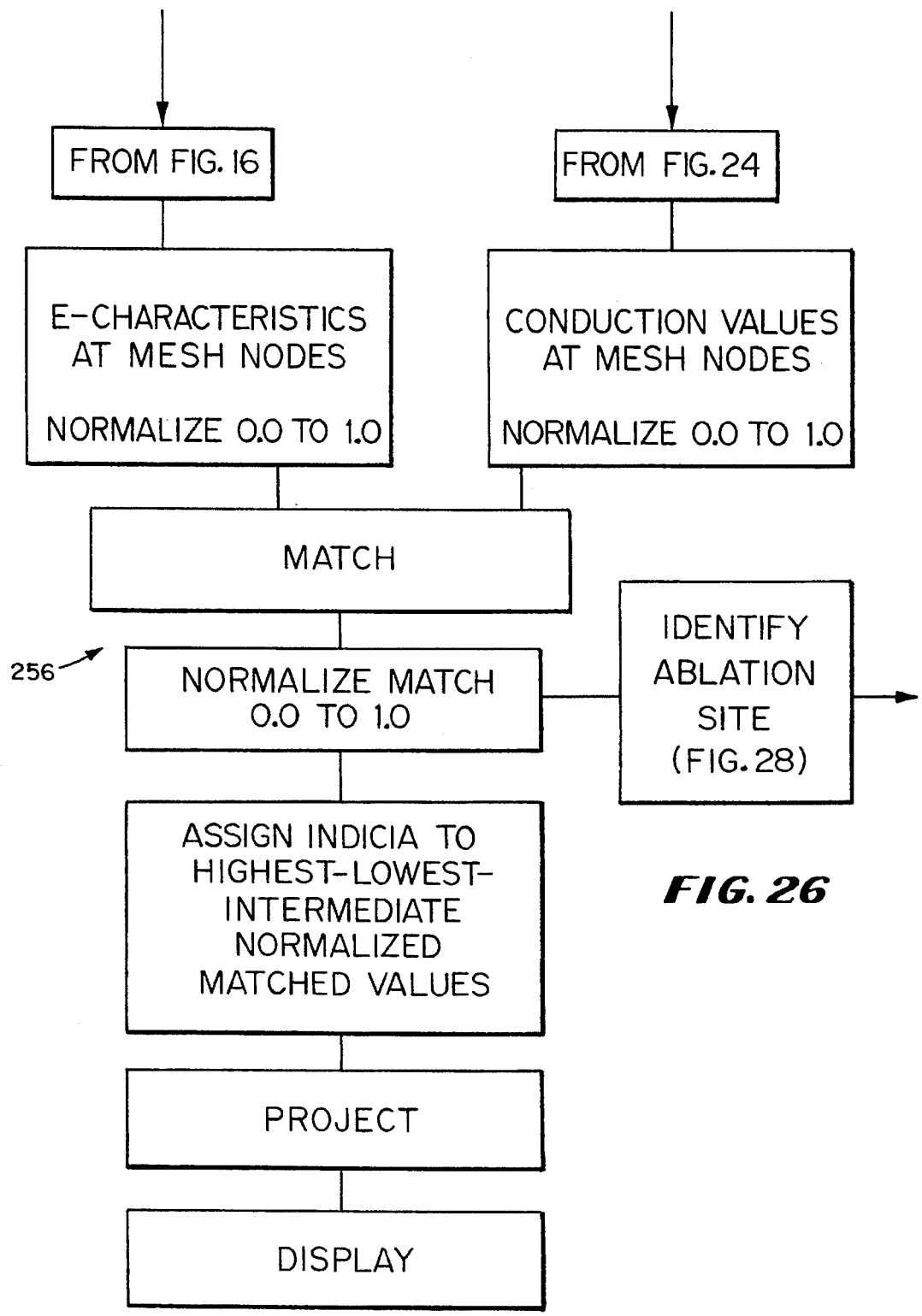
FIG. 26 is a flow chart showing the operation of the means for matching iso-E-Characteristics with iso-conduction information.

FIG. 26 shows the means 256 for matching the iso-conduction with the iso-E-Characteristic for the analyzed heart tissue.

The means 256 derives the values of the E-Characteristic at the nodes of three dimensional mesh in the same manner already described. Next, the means 256 normalizes these E-Characteristic values into an array of numbers from 0.0 to 1.0. The number 1.0 is assigned to the absolute lowest E-Characteristic value, and the number 0.0 is assigned to the absolute highest E-Characteristic value. E-Characteristic values between the absolute lowest and highest values are assigned numbers on a linear scale between the lowest and highest values.

The means 256 also derives the values of the computed electrogram event at the nodes of three dimensional mesh in the manner already described. The means 256 computes the inverse of the magnitude of spatial gradient of the computed electrogram event, as previously described, to derive the value of the conduction of the cardiac signal in the examined tissue.

The means 256 then normalizes these conduction values into an array of numbers from 0.0 to 1.0. The number 1.0 is assigned to the absolute lowest conduction value, and the number 0.0 is assigned to the threshold conduction value. As before, conduction values between the absolute lowest and highest values are assigned numbers on a linear scale between the lowest and highest values.

The means 256 then applies, using known mathematical computational techniques, a two dimensional matched filtering process to the normalized conduction data using the normalized E-Characteristic data as a template, or vice versa. Alternatively, a two dimensional cross-correlation can be applied to the normalized E-Characteristic and conduction. As used in this Specification, "matching" encompasses both two dimensional matched filtering, two dimensional cross-correlation, and a like digital signal processing techniques.

The values obtained from the matched filtering process are normalized, by dividing each value by the maximum absolute value. After normalization, the value will range between 0.0 and 1.0.

The means 256 creates a display by assigning one color the highest normalized matched filter value and another color to the lowest normalized matched filter value. Computer generated hues are assigned to intermediate values, based upon a linear scale, as above described.

The means 256 projects the generated color map upon the basket surface, based upon location of the nodes in the three dimensional mesh.

FIG. 27 shows a representative display processed according to the above methodology. The CPU 206 generates this display on the display device 246 for viewing by the physician.

The display matches the normalized isoconduction values with the normalized iso-E-Characteristic values, in effect matching electrograms with tissue E-Characteristics. This matching provides more precise differentiation between regions of infarcted tissue and regions of healthy tissue.

This information can be further processed to identify a potential ablation site to maximize the CIR.

(v) Identifying a Potential Ablation Site

Figure 28:
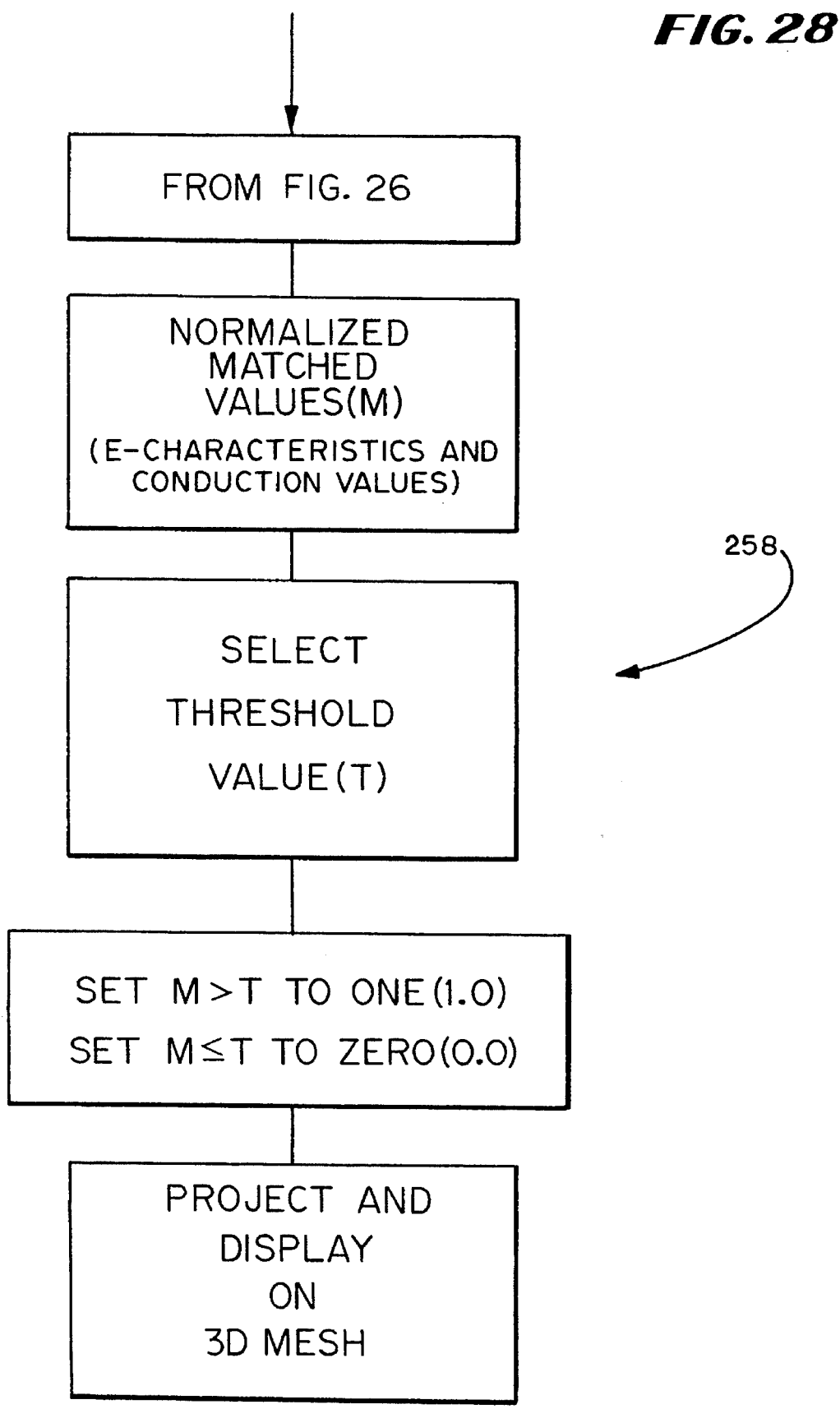
FIG. 28 is a flow chart showing the operation of the means for detecting a possible ablation site based upon the information obtain in FIG. 26.

FIG. 28 shows a means 258 for identifying a potential ablation site based upon the matched output of the normalized conduction values and the normalized E-Characteristic values, generated by the means 256.

The means 258 selects a threshold value. Tissue regions having matched output values above the threshold constitute potential ablation sites. Locating an optimal threshold value can be done by empirical study or modeling. The threshold value for a given set of data will also depend upon the professional judgment of the physician.

Figure 29:
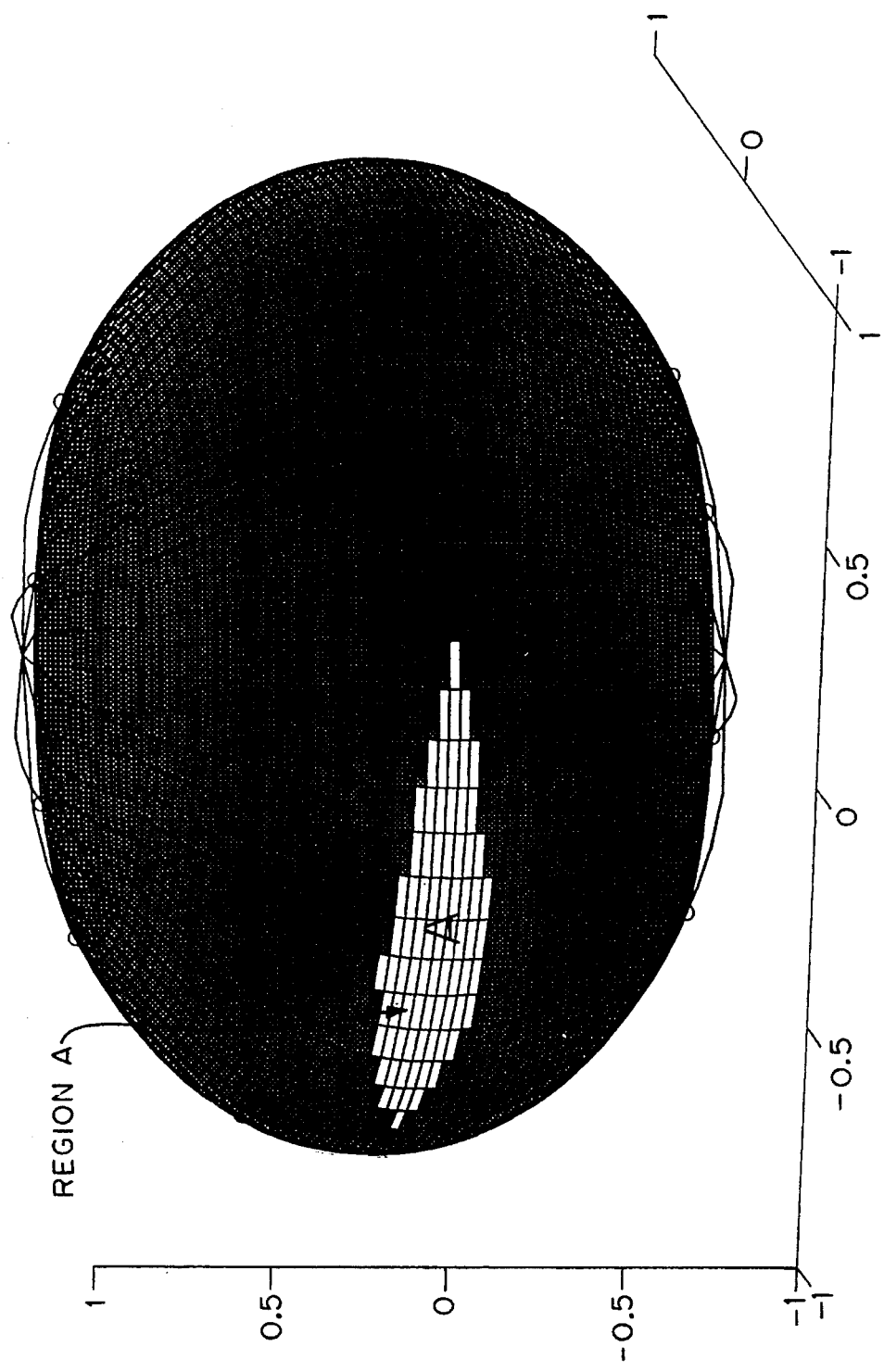
FIG. 29 is a representative display of the matched Iso-E-Characteristics and iso-conduction information, after selection of a threshold value, identifying a potential ablation site.

FIG. 29 shows a representative display processed according to the above methodology. In FIG. 29, a threshold of 0.8 has been used for illustration purposes. Values greater than the threshold of 0.8 have been set to 1.0, while values equal to or less than 0.8 have been set to 0.0. The CPU 206 generates this display on the display device 246 for viewing by the physician.

FIG. 29 provides by sharp contrast between black and white (with no intermediate hues) the potential ablation site (Area A).

E. Ablating the Tissue

Regardless of the specific form of the output used, the physician analyses one or more of the outputs derived from the basket electrodes 38 to locate likely efficacious sites for ablation.

The physician can now takes steps to ablate the myocardial tissue areas located by the basket electrodes 38. The physician can accomplish this result by using an electrode to thermally destroy myocardial tissue, either by heating or cooling the tissue. Alternatively, the physician can inject a chemical substance that destroys myocardial tissue. The physician can use other means for destroying myocardial tissue as well.

Figure 30:
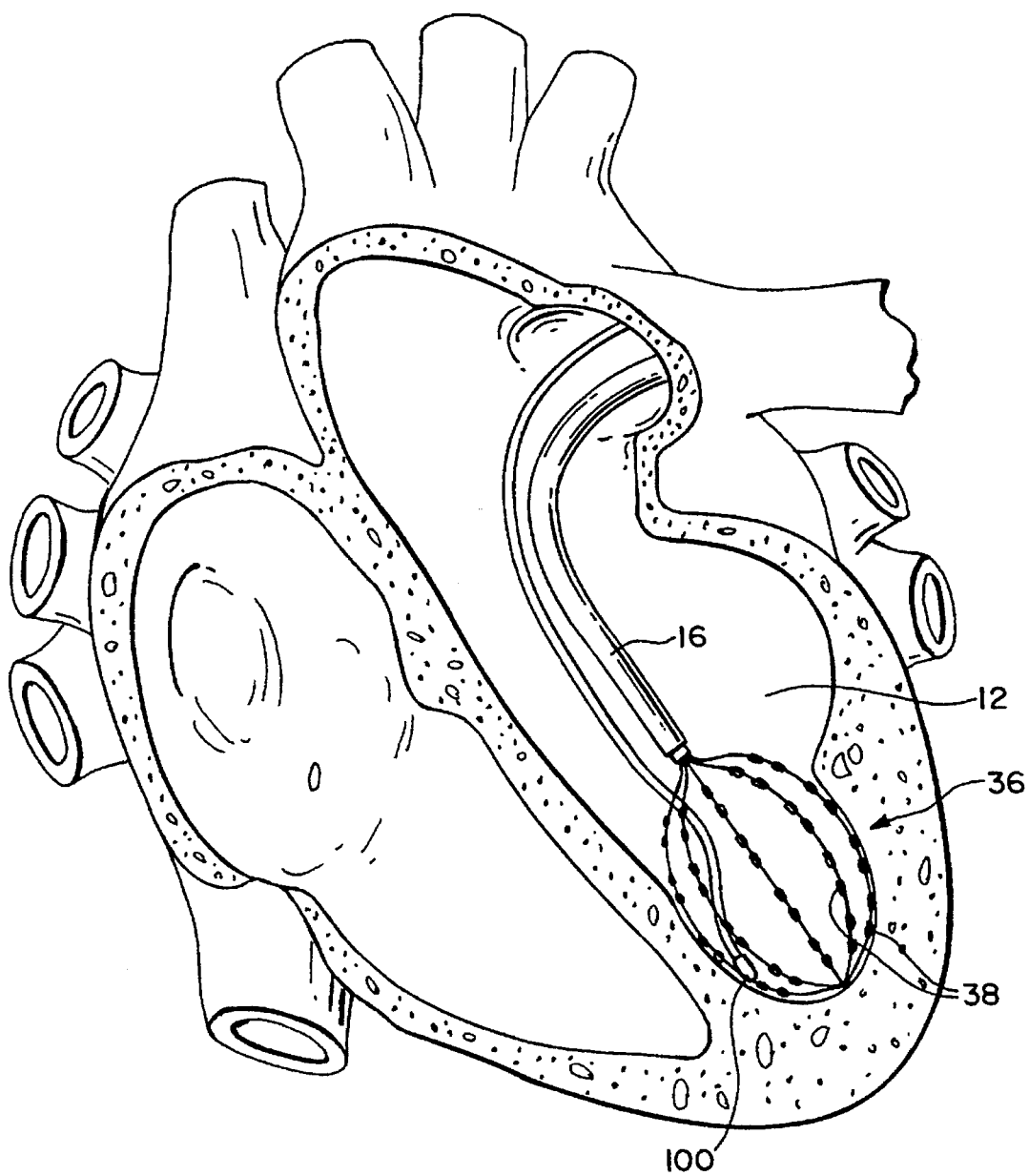
FIG. 30 is a plan view of an ablation probe being used in association with the system shown in FIG. 1.

In the illustrated embodiment (see FIG. 30), an external steerable ablating probe 100 is deployed in association with the basket structure 36.

Various features of the invention are set forth in the following claims.

We claim:

1. A system for examining heart tissue comprising
   at least three spaced apart electrodes,
   locating means for positioning at least two of the electrodes in contact with a heart tissue region,
   first means for transmitting electrical current in a first path through the heart tissue region between a first pair of the electrodes, for transmitting electrical current in a second path through the heart tissue region between a second pair of the electrodes, and for deriving therefrom tissue electrical characteristics based, at least in part, upon sensing impedances of tissue lying in the first and second paths,
   second means for sensing timing of local depolarization events in the tissue in which impedance is sensed and for deriving therefrom propagation velocities of the sensed depolarization events, and
   third means for matching derived tissue electrical characteristics with derived propagation velocities in spatial relation to the electrodes to characterize morphology of heart tissue in the heart tissue region.

2. A system according to claim 1
   and further including means for outputting the match between derived tissue electrical characteristic and derived propagation velocities in spatial relation to the electrodes.

3. A system for examining heart tissue comprising
   at least three spaced apart electrodes,
   locating means for positioning at least two of the electrodes in contact with a heart tissue region,
   first means for transmitting electrical current in a first path through the heart tissue region between a first pair of the electrodes, for transmitting electrical current in a second path through the heart tissue between a second pair of the electrodes, and for deriving therefrom resistivities of the tissue lying in the first and second paths,
   second means for sensing timing of local depolarization events in the tissue in which resistivities is sensed and for deriving therefrom propagation velocities of the sensed depolarization events, and
   third means for matching derived tissue resistivities with derived propagation velocities in spatial relation to the electrodes to characterize morphology of heart tissue in the heart tissue region.

4. A system according to claim 3
   and further including means for outputting the match between derived tissue resistivities and derived propagation velocities in spatial relation to the electrodes.

5. A system for examining heart tissue comprising
   at least three spaced apart electrodes,
   locating means for positioning at least two of the electrodes in contact with a heart tissue region,
   first means for transmitting electrical current in a first path through the heart tissue region between a first pair of the electrodes, for transmitting electrical current in a second path through the heart tissue region between a second pair of the electrodes, and for deriving therefrom tissue electrical characteristics based, at least in part, upon sensing impedances of tissue lying in the first and second paths,
   second means for sensing the timing of local depolarization events in the tissue in which impedance is sensed and for deriving therefrom propagation velocities of the sensed depolarization events, and
   third means for creating matched values that match derived tissue electrical characteristics with derived propagation velocities in spatial relation to the electrodes to characterize morphology of heart tissue in the heart tissue region, the third means including means for outputting the matched values in groups of equal matched values in spatial relation to the electrodes.

6. A system according to claim 5
   wherein the matched values range in value in spatial relation to the electrodes, and
   wherein for third means normalizes the value range to a normalized range of 0.0 to 1.0 in spatial relation to the electrodes by dividing each matched value in the value range by a maximum matched value in the value range.

7. A system according to claim 6
   wherein the third means outputs the normalized matched values in groups of equal matched values in spatial relation to the electrodes.

8. A system for examining heart tissue comprising
   at least three spaced apart electrodes,
   locating means for positioning at least two of the electrodes in contact with a heart tissue region,
   first means for transmitting electrical current in a first path through the heart tissue region between a first pair of the electrodes, for transmitting electrical current in a second path through heart tissue in the region between a second pair of the electrodes, and for deriving therefrom tissue electrical characteristics based, at least in part, upon sensing impedances of tissue lying in the first and second paths, second means for sensing timing of local depolarization events in the tissue in which impedance is sensed and for deriving therefrom propagation velocities of the sensed depolarization events, and third means for normalizing derived tissue electrical characteristics in spatial relation to the electrodes, for normalizing derived propagation velocities in spatial relation to the electrodes, and for matching the normalized derived electrical characteristics with the normalized derived propagation velocities in spatial relation to the electrodes to characterize morphology of heart tissue in the heart tissue region.

9. A system according to claim 8 wherein the third means applies two dimensional matched filtering to the normalized derived tissue electrical characteristics using the normalized propagation velocities as a template.

10. A system according to claim 8 wherein the third means applies two dimensional matched filtering to the normalized derived propagation velocities using the normalized tissue electrical characteristics as a template.

11. A system according to claim 9 or 10 wherein the two dimensional matched filtering provides a matched filter value range including matched filter values ranging in spatial relation to the electrodes, the matched filter value range including a maximum matched filter value, and wherein the third means normalizes the matched filter values to a range of 0.0 to 1.0 in spatial relation to the electrodes by dividing each matched filter value in the matched filter value range by the maximum matched filter value in the matched filter value range.

12. A system according to claim 11 the third means including means for outputting the normalized matched filter values in groups of equal matched normalized matched filter values in spatial relation to the electrodes.

13. A method for examining heart tissue comprising the steps of locating at least three spaced apart electrodes so that at least two of the electrodes are in contact with a heart tissue region, transmitting electrical current in a first path through the heart tissue region between a first pair of the electrodes, transmitting electrical current in a second path through heart tissue region between a second pair of the electrodes, deriving from electrical current transmissions tissue electrical characteristics based, at least in part, upon sensing impedances of tissue lying in the first and second paths, sensing timing of local depolarization events in the tissue in which impedance is sensed and deriving therefrom propagation velocities of the sensed depolarization events, and matching derived tissue electrical characteristics with derived propagation velocities in spatial relation to the electrodes to characterize morphology of heart tissue in the heart tissue region.

14. A method according to claim 13 wherein the matching step includes normalizing the derived tissue electrical characteristics in spatial relation to the electrodes, normalizing the derived propagation velocities in spatial relation to the electrodes, and matching the normalized derived electrical characteristics with the normalized derived propagation velocities in spatial relation to the electrodes.

15. A method for examining heart tissue comprising the steps of locating at least three spaced apart electrodes so that at least two of the electrodes are in contact with a heart tissue region, transmitting electrical current in a first path through the heart tissue region between a first pair of the electrodes, transmitting electrical current in a second path through the heart tissue region between a second pair of the electrodes, deriving from electric current transmissions resistivities of tissue lying in the first and second paths, sensing timing of local depolarization events in the tissue in which resistivities is sensed and deriving therefrom propagation velocities of the sensed depolarization events, and matching derived tissue resistivities with derived propagation velocities in spatial relation to the electrodes to characterize morphology of heart tissue in the heart tissue region.

16. A method according to claim 15 wherein the matching step includes normalizing the derived tissue resistivities in spatial relation to the electrodes, normalizing the derived propagation velocities in spatial relation to the electrodes, and matching the normalized derived tissue resistivities with the normalized derived propagation velocities in spatial relation to the electrodes.

17. A method for examining heart tissue comprising the steps of locating at least three spaced apart electrodes so that at least two of the electrodes are contact with a heart tissue region, transmitting electrical current in a first path through the heart tissue region between a first pair of the electrodes, transmitting electrical current in a second path through the heart tissue between a second pair of the electrodes, deriving from electrical current transmissions tissue electrical characteristics based, at least in part, upon sensing impedances of tissue lying in the first and second paths, sensing timing of local depolarization events in the tissue in which impedance is sensed and deriving therefrom propagation velocities of the sensed depolarization events, and normalizing derived tissue electrical characteristics in spatial relation to the electrodes, normalizing derived propagation velocities in spatial relation to the electrodes, matching the normalized derived electrical characteristics with the normalized derived propagation velocities in spatial relation to the electrodes to characterize morphology of heart tissue in the heart tissue region by applying two dimensional matched filtering to the normalized derived tissue electrical characteristics using the normalized propagation velocities as a template, or vice versa.

18. A method according to claim 17 wherein the matching step provides matched filter values ranging in spatial relation to the electrodes, and wherein the matching step further normalizes the matched filter values to a range of 0.0 to 1.0 in spatial relation to the electrodes by dividing each matched filter value in the matched filter value range by the maximum matched filter value in the matched filter value range.

19. A method according to claim 18 and further including the step of outputting the normalized matched filter values in groups of equal matched normalized matched filter values in spatial relation to the electrodes.

* * * * *